(12) United States Patent
Chan et al.

(10) Patent No.: US 11,096,606 B2
(45) Date of Patent: *Aug. 24, 2021

(54) DETERMINING BODY POSTURES AND ACTIVITIES

(71) Applicant: Vital Connect, Inc., San Jose, CA (US)

(72) Inventors: Alexander Chan, Campbell, CA (US); Nima Ferdosi, San Jose, CA (US); Ravi Narasimhan, Sunnyvale, CA (US)

(73) Assignee: Vital Connect, Inc., San Jose, CA (US)

( * ) Notice: Subject to any disclaimer, the term of this patent is extended or adjusted under 35 U.S.C. 154(b) by 415 days.

This patent is subject to a terminal disclaimer.

(21) Appl. No.: 16/003,137

(22) Filed: Jun. 8, 2018

(65) Prior Publication Data

US 2018/0289289 A1 Oct. 11, 2018

Related U.S. Application Data

(63) Continuation of application No. 14/069,099, filed on Oct. 31, 2013, now Pat. No. 9,999,376.

(Continued)

(51) Int. Cl.
*A61B 5/11* (2006.01)
*G01C 22/00* (2006.01)
*A61B 5/00* (2006.01)

(52) U.S. Cl.
CPC ............ *A61B 5/1116* (2013.01); *A61B 5/1118* (2013.01); *A61B 5/0004* (2013.01);
(Continued)

(58) Field of Classification Search
CPC .......... A61B 2562/0219; A61B 5/1116; A61B 5/1117; A61B 5/1118; A61B 5/112;
(Continued)

(56) References Cited

U.S. PATENT DOCUMENTS

| 7,423,537 | B2 * | 9/2008 | Bonnet ................. A61B 5/1117 340/573.1 |
| 8,206,325 | B1 * | 6/2012 | Najafi ................... A61B 5/1116 600/595 |

(Continued)

FOREIGN PATENT DOCUMENTS

| WO | WO 2011/133799 A1 | 10/2011 |
| WO | WO 2012/014110 A2 | 2/2012 |

OTHER PUBLICATIONS

Extended European Search Report from EP Application No. 19179992.3 dated Sep. 30, 2019, 7 pages.

(Continued)

*Primary Examiner* — David J. McCrosky
(74) *Attorney, Agent, or Firm* — Brundidge & Stanger, P.C.

(57) ABSTRACT

A method and wireless sensor device for determining body postures and activities. In one aspect, a method includes receiving sensor data. The method also includes detecting and classifying a body transition of a body based on the sensor data. The method also includes detecting if there is activity of the body based on the sensor data. If there is activity, the method also includes classifying the activity. If there is no activity, the method also includes classifying a rest position of the body based on the sensor data and based on a previous body transition.

16 Claims, 27 Drawing Sheets

Related U.S. Application Data

(60) Provisional application No. 61/722,069, filed on Nov. 2, 2012.

(52) U.S. Cl.
CPC ........... *A61B 5/1123* (2013.01); *A61B 5/6823* (2013.01); *A61B 5/7264* (2013.01); *A61B 2505/09* (2013.01); *A61B 2560/0223* (2013.01); *A61B 2562/0219* (2013.01); *G01C 22/006* (2013.01)

(58) Field of Classification Search
CPC ... A61B 5/1121; A61B 5/1122; A61B 5/1123; A61B 5/1126; A61B 5/1127; A61B 5/1128; A61B 2503/08; A61B 2503/10; A61B 2503/12; A61B 2503/20; A61B 2503/22; A61B 2503/24; A61B 2503/00; G08B 21/0446
See application file for complete search history.

(56) References Cited

U.S. PATENT DOCUMENTS

| | | |
|---|---|---|
| 2005/0172311 A1 | 8/2005 | Hjelt et al. |
| 2007/0118056 A1 | 5/2007 | Wang et al. |
| 2009/0082699 A1 | 3/2009 | Bang et al. |
| 2010/0217533 A1 | 8/2010 | Nadkarni et al. |
| 2010/0256532 A1 | 10/2010 | Nishibayashi |
| 2010/0298655 A1 | 11/2010 | McCombie et al. |
| 2011/0054359 A1 | 3/2011 | Sazonov et al. |
| 2011/0066383 A1 | 3/2011 | Jangle et al. |
| 2013/0116602 A1* | 5/2013 | Van Den Heuvel ......................... A61B 5/1126 600/595 |

OTHER PUBLICATIONS

Extended European Search Report from EP Application No. 19179988.1 dated Sep. 30, 2019, 8 pages.
The International Search Report and the Written Opinion of the International Searching Authority issued for International Application No. PCT/US2013/068097, dated Mar. 27, 2014.
Karantonis D. M., et al "Implementation of a Real-time Human Movement Classifier using a Triaxial Accelerometer for Ambulatory Monitoring", IEEE Transactions on Information Technology in Boimedicine, IEEE Service Center, Los Alamitos, CA, vol. 10, No. 1, Jan. 1, 2006, pp. 156-167.
European Search Report dated Jun. 6, 2016.
Mathie, M. J., et al, "Detection of daily physical activities using a triaxial accelerometer," Medical and Biological Engineering and Computing 41.3 (2003):296-301. (Year:2003).
Mathie, M. J., et al, "Classification of basic daily movements using a triaxial accelerometer," Medical and Biological Engineering and Computing 42.5(2004):679-687, (Year:2004).

* cited by examiner

DETERMINING BODY POSTURES AND ACTIVITIES

CROSS-REFERENCE TO RELATED APPLICATIONS

This Application is a Continuation of U.S. application Ser. No. 14/069,099, filed Oct. 31, 2013, which claims the benefit of U.S. Provisional Application No. 61/722,069, filed Nov. 2, 2012, which are hereby incorporated by reference in their entirety, and is related to the U.S. application Ser. No. 16/003,138, filed Jun. 6, 2018, which is a Continuation of U.S. application Ser. No. 14/069,099, filed Oct. 31, 2013, which claims the benefit of U.S. Provisional Application No. 61/722,069, filed Nov. 2, 2012.

FIELD OF THE INVENTION

The present invention relates generally to wireless sensor devices, and more particularly to a wireless sensor device for determining body postures and activities.

BACKGROUND

Wireless sensor devices are used in a variety of applications including posture detection and activity monitoring of users. In many of these applications, a wireless sensor device is attached directly to the user's skin (e.g., near the chest area) to measure certain data. This measured data is then utilized for the posture detection and activity monitoring of the users. There is a strong need for a cost-effective solution that overcomes the aforementioned issues. The present invention addresses such a need.

SUMMARY

A method and wireless sensor device for determining body postures and activities are disclosed. In one aspect, a method includes receiving sensor data. The method also includes detecting and classifying a posture transition of a body based on the sensor data. The method also includes detecting if there is activity of the body based on the sensor data. If there is activity, the method also includes classifying the activity. If there is no activity, the method also includes classifying a rest position of the body based on the sensor data and based on a previous posture transition.

In another aspect, a body sensor device includes a processor and a memory device coupled to the processor. The body sensor device includes an application that, when executed by the processor, causes the processor to perform operations including receiving sensor data; detecting and classifying a body transition of a body based on the sensor data; detecting if there is activity of the body based on the sensor data; if there is activity, classifying the activity; and if there is no activity, classifying a rest position of the body based on the sensor data and based on a previous body transition.

DETAILED DESCRIPTION

The present invention relates generally to wireless sensor devices, and more particularly, to a wireless sensor device for determining body postures and activities of a person. The following description is presented to enable one of ordinary skill in the art to make and use embodiments of the invention, and is provided in the context of a patent application and its requirements. Various modifications to the embodiments and the generic principles and features described herein will be readily apparent to those skilled in the art.

Thus, embodiments of the present invention are not intended to be limited to the examples shown, but are to be accorded the widest scope consistent with the principles and features described herein.

Embodiments provide a method and system for determining body postures and activities of a person. As described in more detail below, a body sensor device receives sensor data. The body sensor device then detects and classifies a body transition of a body based on the sensor data. The body sensor device then detects if there is activity of the body based on the sensor data. If there is activity, the body sensor device classifies the activity. If there is no activity, the body sensor device classifies a rest position of the body based on the sensor data and based on a previous body transition.

Figure 1:
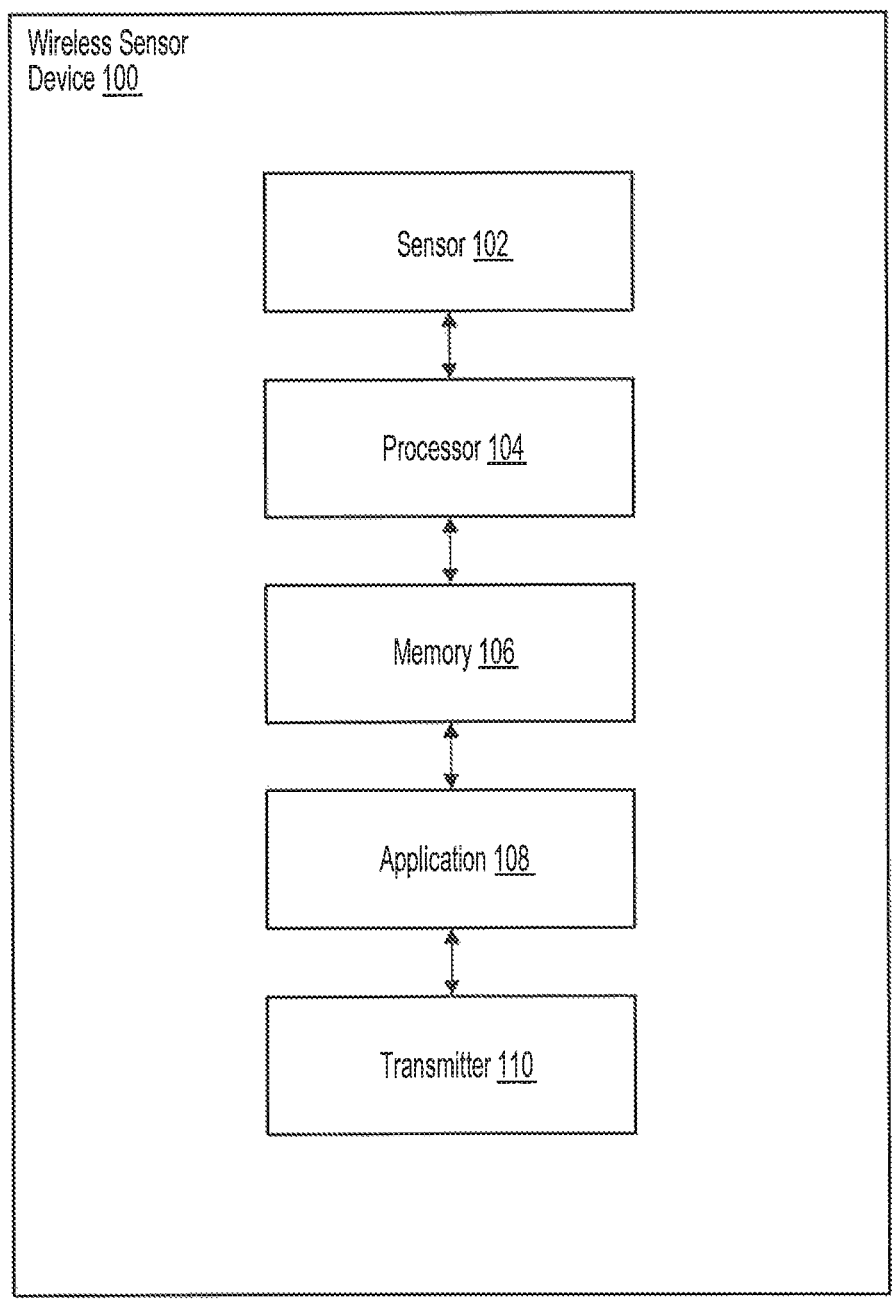
FIG. 1 illustrates a wireless sensor device in accordance with an embodiment.

FIG. 1 illustrates a wireless sensor device 100 in accordance with an embodiment. As shown, the wireless sensor device 100 includes a sensor 102, a processor 104 coupled to the sensor 102, a memory 106 coupled to the processor 104, an application 108 coupled to the memory 106, and a transmitter 110 coupled to the application 108. The wireless sensor device 100 may be used to implement a body sensor device. In one embodiment, the wireless sensor device 100 is attached, in any orientation to a user and on any location of the user. In one embodiment, the wireless sensor device 100 is chest- or torso- or thorax-mounted to the user. The sensor 102 obtains data from the user and transmits the data to the memory 106 and in turn to the application 108. The processor 104 executes the application 108 to monitor information regarding the user's posture and activity levels. The information is transmitted to the transmitter 110 and in turn relayed to another user or device.

In one embodiment, the sensor 102 is a microelectromechanical system (MEMS) tri-axial accelerometer and the processor 104 is a microprocessor. One of ordinary skill in the art readily recognizes that a variety of devices can be utilized for the processor 104, the memory 106, the application 108, and the transmitter 110 and that would be within the spirit and scope of the present invention.

In one embodiment, the wireless sensor device is a triaxial accelerometer. One of ordinary skill in the art readily recognizes that a variety of wireless sensor devices can be utilized. For example, various embodiments, the wireless sensor device may be at least one of a triaxial accelerometer, a uni-axial accelerometers, a bi-axial accelerometers, a gyroscope, a pressure sensor, a patch form-factor, etc., all of which would be within the spirit and scope of the embodiments of the present invention.

In one embodiment, the acceleration samples are calibrated. Conventionally, a wireless sensor device that only utilizes non-calibrated accelerometer data leads to less accurate posture detection and activity level monitoring. Non-calibrated accelerometer data can be arbitrarily positioned relative to the actual body axes. Therefore, embodiments described herein may involve a calibration procedure of the wireless sensor device that enables the generation of three derived axes of acceleration data that line up with actual body axes: anterior-posterior AP (front-to-back)—Z-axis; medial-lateral ML (left-to-right)—X-axis; and vertical VT (head-to-toe)—Y-axis. The calibration procedure requires determining at least the direction of the VT axis before the VT axis is then used to determine the other 2 axes. In another embodiment, additional calibration during leaning forward or lying supine is utilized to improve calibration accuracy.

Embodiments calibrate a wireless sensor device via automatic calibration, manual calibration, and sleep study calibration. In automatic calibration, an algorithm analyzes whether the user is walking and then obtains a vertical calibration vector during this detected walking period. In manual calibration, there is a wireless communication between the patch form-factor wireless sensor device and a relay (e.g., smartphone, handheld device, computer, communication device) that manually calibrates the wireless sensor device when selected or when automatic calibration fails. Manual calibration includes but is not limited to single upright calibration, walking calibration, upright and leaning forward calibration for improved accuracy, and supine and sitting up calibration for bedridden patients. In sleep study calibration, if only sleep data when the user is lying down is available (e.g. during a sleep study), an algorithm automatically calibrates the wireless sensor device given a whole night of data.

Embodiments determine a vertical axis VT and use the VT to determine the other 2 axes. If manual calibration is selected, all of the microelectromechanical systems (MEMS) based algorithms of the wireless sensor device utilize the manual calibration to detect posture and activity levels of the user. If automatic calibration is selected, all of the MEMS based algorithms of the wireless sensor device utilize the automatic calibration to detect posture and activity levels of the user. If neither manual calibration nor automatic calibration is selected, posture detection is disabled and all of the MEMS based algorithms of the wireless sensor device operate in non-calibrated mode.

Once automatic calibration of the wireless sensor device is achieved, the derived calibration vector enables the wireless sensor device to utilize various algorithms that measure the user's activity levels including but not limited to pedometer step-counting, fall detection, and posture detection. In one embodiment, after attaching the wireless sensor device to the user, the wireless sensor device continuously and automatically obtains varying types of data including but not limited to acceleration samples along at least one axis of the user. An application embedded within a processor of the wireless sensor device compares the acceleration samples to a threshold to measure the user's activity levels.

Figure 2:
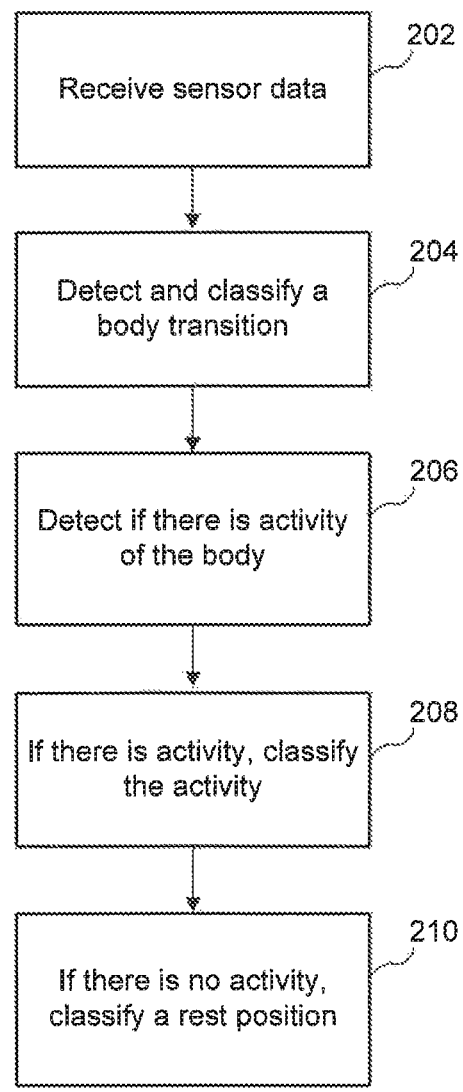
FIG. 2 illustrates a method for determining body postures and activities in accordance with an embodiment.

FIG. 2 illustrates a method for determining body postures and activities in accordance with an embodiment. Referring to FIGS. 1 and 2 together, first, the wireless sensor device 100 receives sensor data, via step 202. In one embodiment, the sensor data includes acceleration samples in relation to at least one axis associated with a person's body over a predetermined time window. In one embodiment, the wireless sensor device 100 calibrates the sensor data such that axes of the sensor match axes of a body.

The wireless sensor device 100 then detects and classifies a posture transition of a body based on the sensor data, via step 204. In one embodiment, to detect the posture transition, the wireless sensor device 100 detects if the body is transitioning from a first posture to a second posture.

The wireless sensor device 100 then detects if there is activity of the body based on the sensor data, via step 206. In one embodiment, to detect the body transition, the wireless sensor device 100 computes a transition signal, and then determines if the transition signal exceeds a transition threshold. If the transition signal exceeds the transition threshold, the wireless sensor device classifies if the posture transition is a particular posture transition. In one embodiment, the posture transition is one of sitting-to-standing, standing-to-sitting, or bending over.

If there is activity of the body, the wireless sensor 100 device then classifies the activity, via step 208. In one embodiment, to detect if there is activity of the body, the wireless sensor device 100 determines a signal magnitude area of the accelerometer signals. The wireless sensor device 100 then determines if the signal magnitude area is greater than an activity threshold. In one embodiment, the activity is one of walking or running.

If there is no activity of the body, the wireless sensor device 100 then classifies a rest position of the body based on the sensor data and based on a previous body transition, via step 210. In one embodiment, to classify the rest position of the body, the wireless sensor device 100 computes a vertical angle, and classifies the rest position based on the vertical angle and a previous body transition. In one embodiment, the rest position is one of sitting, standing, or lying down.

In some embodiments, automatically detecting and classifying posture and activity can be extremely useful for monitoring the daily activity of various populations (e.g., nursing home residents, patients that require physical activity, etc.).

In some embodiments, any type of sensor such as a tri-axial accelerometer can be mounted to the body (e.g., chest, waist, etc.), which is inexpensive and allows for continuous monitoring.

In various embodiments, there are two main parts that constitute a posture/activity classifier. The first part is posture classification, which distinguishes between stationary activities such as sitting, standing, bending over, and lying down (in various subpostures: supine, prone, lateral left, and lateral right). The second part is activity classification, which distinguishes between walking, running, and other types of activities such as driving or cycling, and which counts steps during walking/running.

Posture classification that is based on only body angle is often inaccurate because sitting and standing can look alike. In various embodiments, the system first detects and classifies postural transitions. During rest, the system looks at the last activity, the last transition, and the body angle to determine the most likely posture.

Activity classification can distinguish walking/running from other types of activity (e.g. driving) by looking at: regularity of steps, greater movement in the vertical direction than the horizontal direction, and the left-right swaying movement that appears during walking/running.

Overall Posture/Activity Classification

Figure 3:
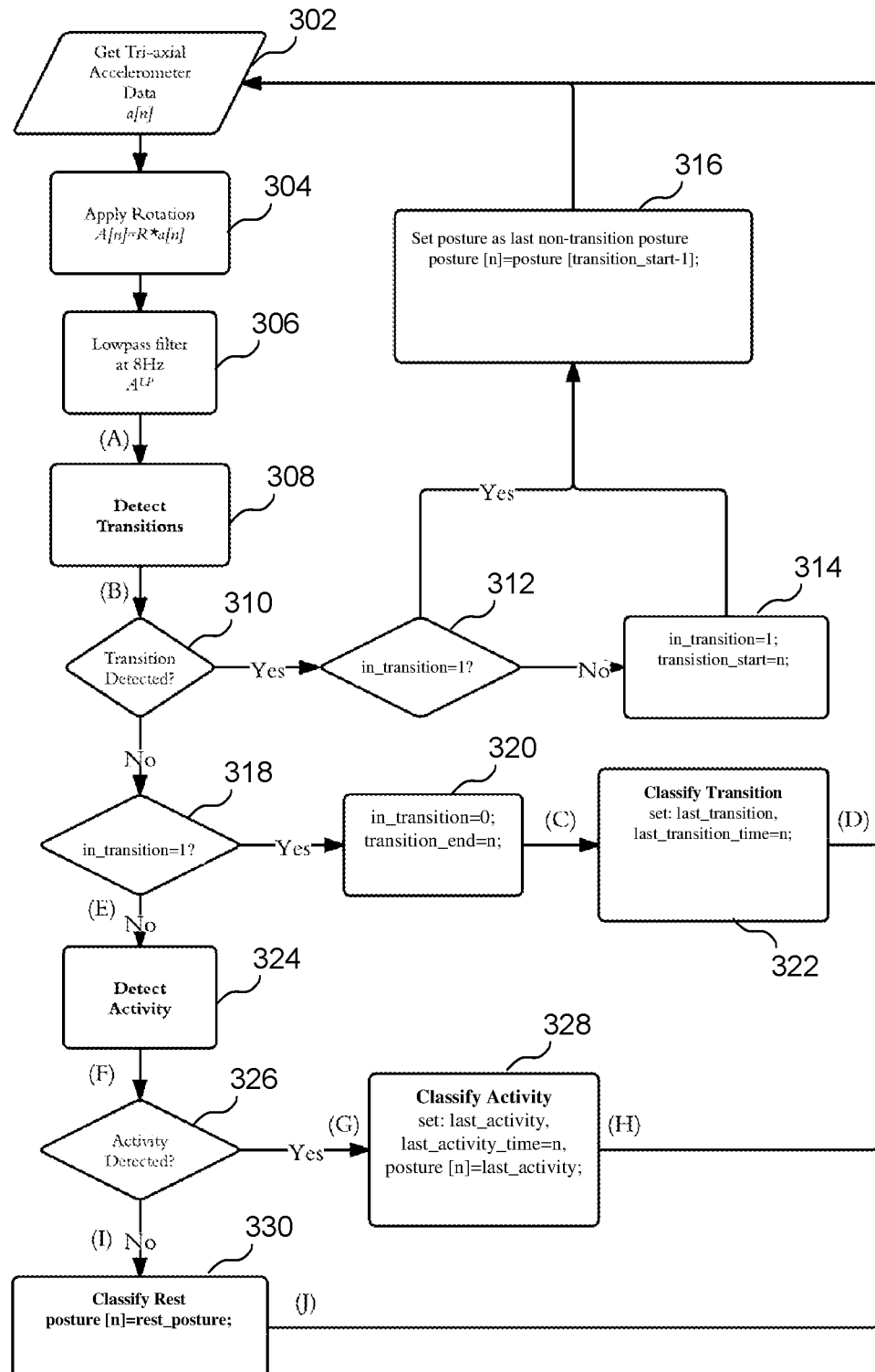
FIG. 3 illustrates a method for determining body postures and activities in accordance with an embodiment.

FIG. 3 illustrates a method for determining body postures and activities in accordance with an embodiment. Referring to FIGS. 1 and 3 together, first, the wireless sensor device 100 obtains tri-axial accelerometer data a[n], via step 302, where a[n] are raw acceleration samples in three axes (x,y,z).

The wireless sensor device 100 then applies a rotation A[n]=R*a[n], via step 304, where A[n] are rotated accelerations in three calibrated axes (x,y,z), and where R is a rotation matrix to transform a[n] to A[n]. In some embodiments, the wireless sensor device 100 applies the rotation of accelerometer axes to match vertical and horizontal body axes. Because the accelerometer can be mounted in any position, it is calibrated during an initial period of standing/walking so that wireless sensor device 100 knows the true body axes, and is calibrated so that X points to the right, Y points up, and Z points backwards.

The wireless sensor device 100 then applies a low-pass filter, via step 306, where $A_{LP}$ are low-pass filtered accelerations.

The wireless sensor device 100 then detects transitions, via step 308. If a transition is detected, via step 310, the wireless sensor device 100 classifies that transition. If a transition is detected, the wireless sensor device 100 sets flags indicating a transition is occurring, via steps 312 and 314. The wireless sensor device 100 then sets the posture as the last non-transition posture, via step 316.

If the wireless sensor device 100 does not detect a transition, via step 310, but flags are set indicating a transition was occurring, via step 318, the wireless sensor device 100 finishes detecting that transition, via step 320, and then classifies it, via step 322. For example, transition classifications may include sit-to-stand, stand-to-sit, and bending over.

If the wireless sensor device 100 was not detecting a transition, and still does not detect a transition, the wireless sensor device 100 then detects activity, via step 324. If there is activity, via step 326, the wireless sensor device 100 classifies it, via step 328. For example, such activity classifications may include walking, running, or other activities.

If there is no activity, the wireless sensor device 100 determines it as a rest period, via step 330, and then classifies the rest period using the previous transition (e.g., uses last transition, last activity, and body angle, etc.). For example, rest classifications may include sitting, standing, lying down (e.g., supine, prone, left lateral, right lateral).

Accordingly, the previously detected transitions and activities are used to determine the posture in the rest periods. In many scenarios, if one observes via sensors when someone is at rest, it is difficult to determine whether the person is sitting or standing. However, if a transition and movement is detected beforehand (e.g., walking and then stopped), the person is most likely standing. If a stand-to-sit transition was detected, and the person is resting with no movement, the person is most likely sitting.

Figure 4:
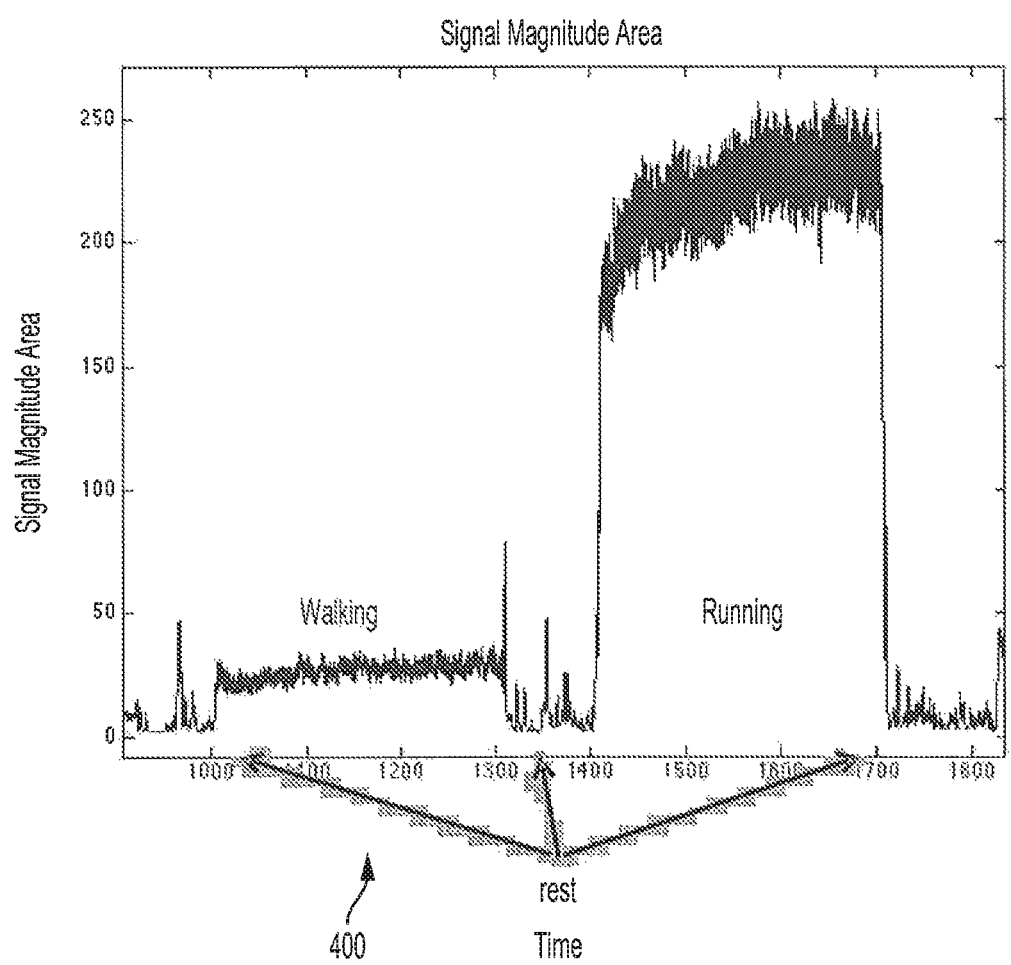
FIG. 4 illustrates a diagram of an example of a graph showing differences in activity between walking and running in accordance with an embodiment.

FIG. 4 illustrates a diagram of an example of a graph 400 showing differences in activity between walking and running in accordance with an embodiment. In one embodiment, detecting activity is done using the signal magnitude area of the accelerometer signals. As shown, walking and running demonstrate different magnitudes of activity, where walking is shown on the left with a smaller magnitude and running is shown on the right with a larger magnitude.

Detecting Activity

Figure 5:
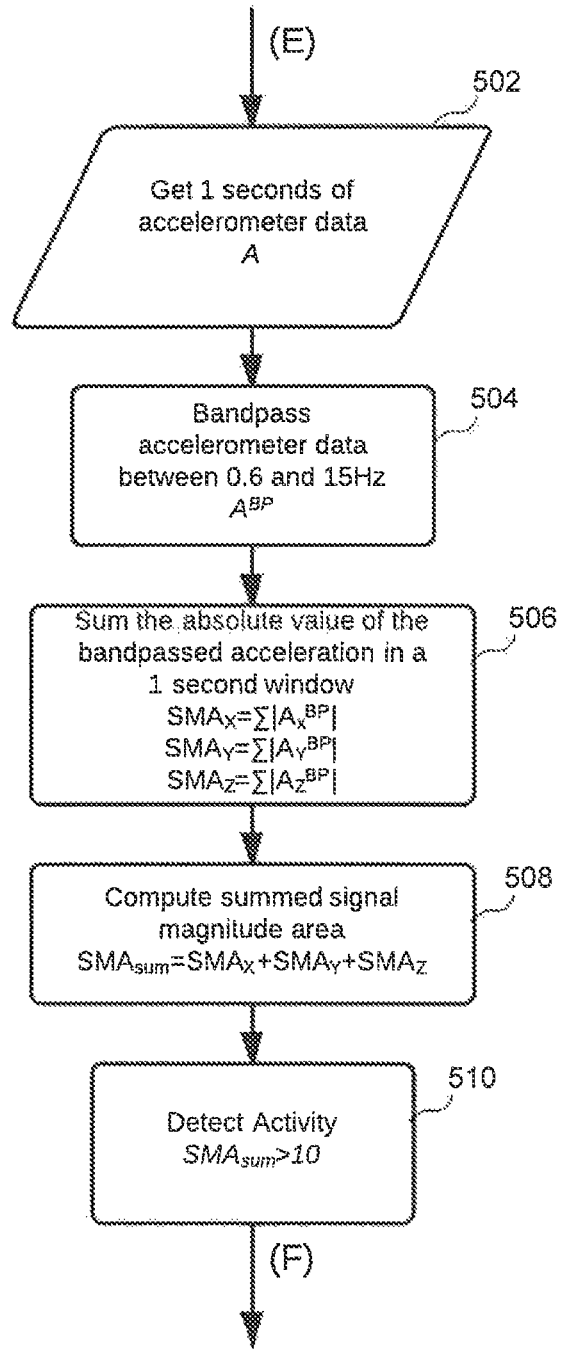
FIG. 5 illustrates a method for detecting activity in accordance with an embodiment.

FIG. 5 illustrates a method for detecting activity in accordance with an embodiment. Referring to FIGS. 3 and 5 the flow chart of FIG. 5 corresponds to step 324 (Detect Activity) of the flow chart of FIG. 3. Referring to FIG. 5, the wireless sensor device 100 obtains accelerometer data (e.g., one second window), via step 502. In one embodiment, a one second window is one second of accelerometer data. The wireless sensor device 100 then applies a band-pass (e.g., between 0.6 and 15 hertz), via step 504. In one embodiment, the accelerometer data on all three axes are bandpass filtered. The wireless sensor device 100 then sums the absolute value of each bandpass filtered acceleration in a window period (e.g., 1 second window), via step 506. The sum of the absolute value of this filtered data within one second is computed for each axis.

The wireless sensor device 100 then computes a summed signal magnitude area ($SMA_{sum}=SMA_X+SMA_Y+SMA_Z$), via step 508. The summed signal magnitude area (SMA) from each axis is added to get the final SMA for that window.

The wireless sensor device 100 then detects activity ($SMA_{sum}>10$), via step 510. In one embodiment, detecting activity is based on a threshold on the signal magnitude area (SMA). An SMA greater than a threshold (in this case 10) is used to detect that activity is occurring. This information then goes onto the activity classifier, which determines what kind of activity is occurring.

Classifying Activity

Figure 6:
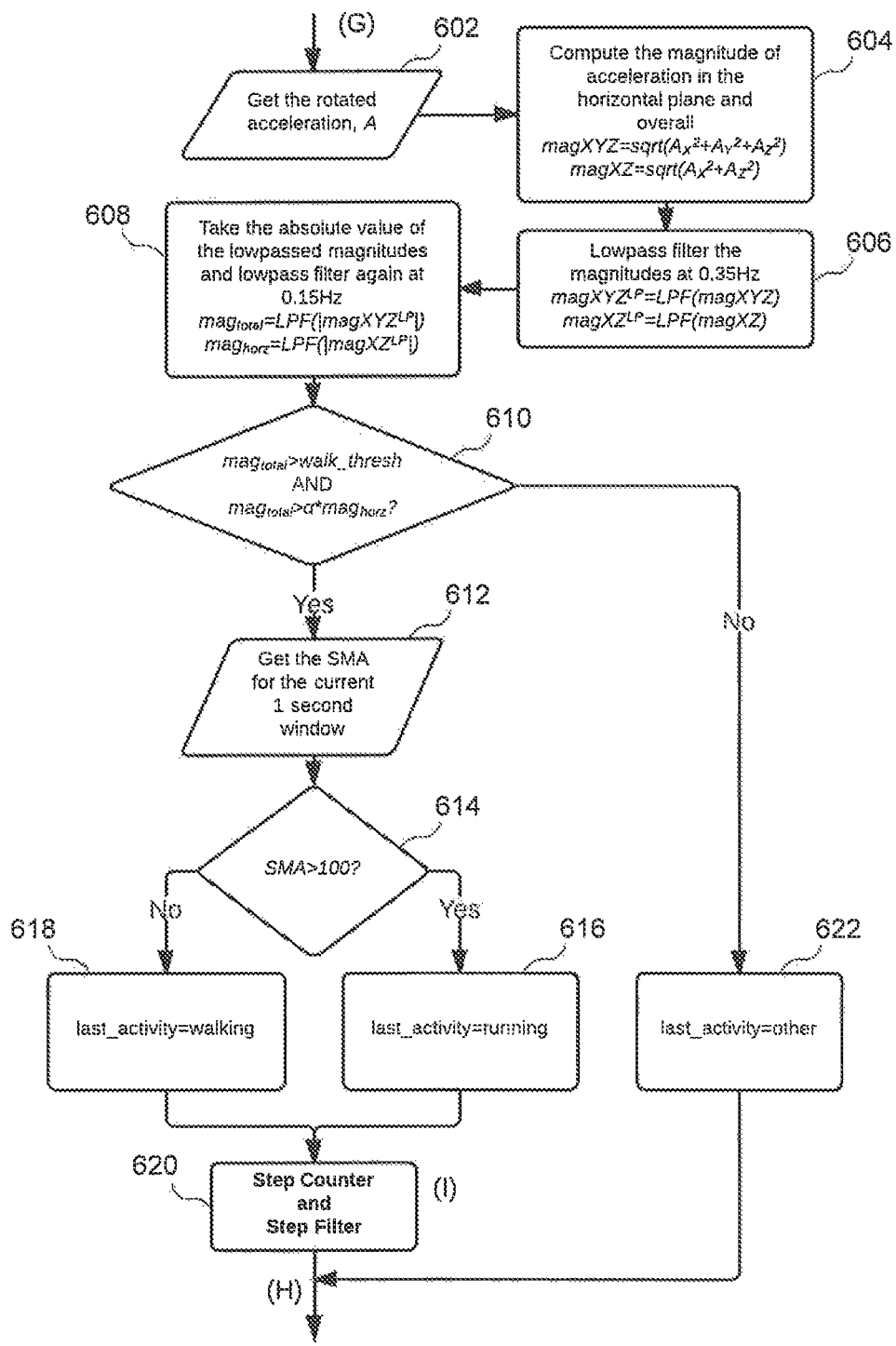
FIG. 6 illustrates a method for classifying activity in accordance with an embodiment.

FIG. 6 illustrates a method for classifying activity in accordance with an embodiment. Referring to FIGS. 3 and 6 the flow chart of FIG. 6 corresponds to step 328 (Classify Activity) of the flow chart of FIG. 3. As described in more detail below, to filter out activities that are not walking or running (e.g., driving, cycling, etc.) the algorithm compares the acceleration in the horizontal directions to the overall magnitude of acceleration. The algorithm also determines the difference between the acceleration in the vertical direction versus the horizontal plane. Activity where the vertical acceleration is larger than the horizontal plane is most likely walking and running.

Referring to FIG. 6, the wireless sensor device 100 obtains rotated acceleration, via step 602. The wireless sensor device 100 computes the magnitude of the accelerations all three directions x,y,z, giving the overall acceleration, via step 604. The magnitude of accelerations in the x and z directions constitute the acceleration in the horizontal plane. The wireless sensor device 100 then applies a low-pass filter to the accelerations, via step 606. The wireless sensor device 100 then takes the absolute value and low-pass filters it again, via step 608. The result is a measure of the overall magnitude of the activity and the magnitude of the accelerations in the horizontal plane.

The wireless sensor device 100 then makes some comparisons. For example, wireless sensor device 100 determines if the total magnitude of activity is greater than some walk threshold, and if the total activity is greater than some constant times the horizontal plane activity, via step 610. In walking and running, the up and down stepping motion makes the overall magnitude of acceleration larger than the acceleration in the horizontal directions ($mag_{total} > \alpha * mag_{horz}$), where $\alpha$ is a constant that determines how much the total magnitude should be larger than the horizontal magnitude, and can be used to adjust the sensitivity (default=1). Also, the total magnitude ($mag_{total}$) should be greater than a threshold walk_thresh.

If the overall acceleration passes those two criteria, the wireless sensor device 100 obtains the SMA for the current window (e.g., 1 second window), via step 612. The SMA is already computed, and is used to determine if the activity is walking or running.

The wireless sensor device 100 then compares SMA to a threshold (e.g., 100 gravity units), via step 614. If this threshold is fulfilled (SMA>100), the activity is defined as running, via step 616. Otherwise it is walking, via step 618.

If the wireless sensor device 100 detects walking or running, the wireless sensor device 100 may put it through a step filter or step counter to count actual steps, via step 620. As described in more detail below, another step-counting algorithm is used to count steps during walking or running.

If the overall acceleration magnitude does not pass those two criteria, then the activity is something else (undetermined), via step 622.

Sitting, Standing, Lying Body Angles

Figure 7:
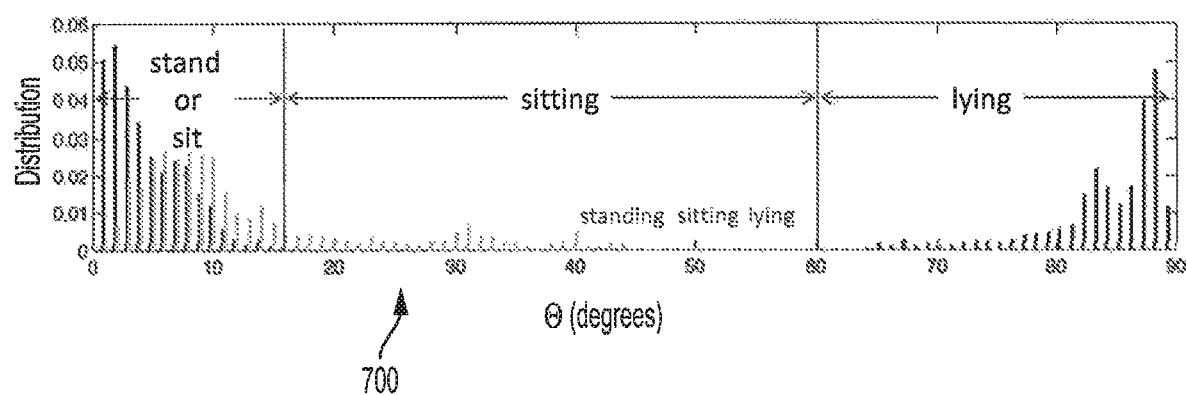
FIG. 7 illustrates a graph showing sitting, standing, and lying body angles in accordance with an embodiment.

FIG. 7 illustrates a graph 700 showing sitting, standing, and lying body angles in accordance with an embodiment. The wireless sensor device 100 can compute a vertical angle, $\theta$ of the torso after obtaining this calibrated acceleration data. The wireless sensor device 100 can compute that as arccosine of the vertical direction. $\theta = \arccos(-A^{LP}_y)$. As such, the y direction is defined to be vertical.

Lying can be detected based on the vertical angle. The wireless sensor device 100 can use a threshold on the vertical angle to perform a classification (e.g., 860° is considered lying). Sitting and standing are highly overlapped, but sitting can occur at more extreme angles than standing ($15° \leq \theta < 60°$ is considered sitting). In some embodiments, the wireless sensor device 100 analyzes transitions to help distinguish between sitting and standing when $\theta < 15°$.

The wireless sensor device 100 can detect particular types of sitting when a body is leaning back, lying on a couch, etc. If the wireless sensor device 100 detects a vertical angle, $\theta$, between 15° and 60°, it is quite certain the body is sitting. However, in a range below 15°, it is hard to determine whether the body is sitting or standing.

Transitions in Triaxial Accelerometers

Figure 8:
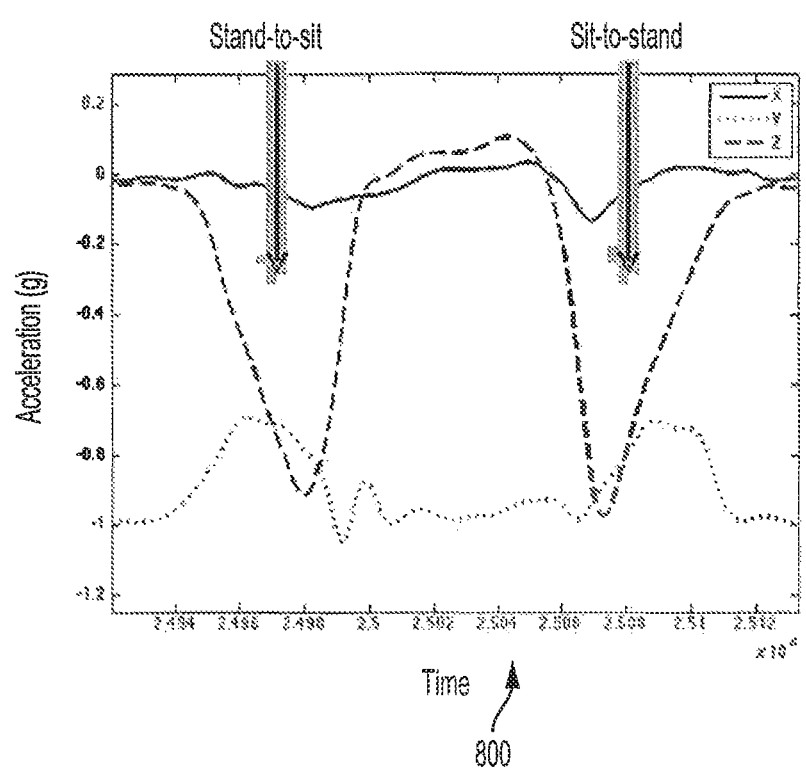
FIG. 8 illustrates a graph showing body transitions in accordance with an embodiment.

FIG. 8 illustrates a graph 800 showing body transitions in accordance with an embodiment. Graph 800 shows x, y, z acceleration data. The horizontal axis is time and the vertical axis is acceleration in g. The 3 lines are x, y, and z accelerometer data. The first large deflection demonstrates the changes in the accelerometer signals when transitioning from standing to sitting. The other large deflection shows transitioning from sitting back to standing again.

Referring to the graph 800, in the very beginning, the body is standing. In the middle, the body is sitting, and at the end the body is standing again. Accordingly, stand to sit, and then sit to stand are the two transitions. When the body sits down, the body leans forward slightly, causing a large change in the z-axis. When the body stands up again, the body leans forward yet again, causing another large change in the z-axis. The very bottom dotted line is y. The dashed line is z. The solid line is x.

As shown, stand-to-sit and sit-to-stand transitions are easily seen on triaxial accelerometers, and are seen as a minima in the z-axis and a maxima in the y-axis. With regard to the stand-to-sit transition, the minima in Z axis (anterior-posterior) comes later than maxima in Y axis (vertical). There is also more area to the left of Z minima than to the right. With regard to the sit-to-stand transition, the minima in Z comes before maxima in Y. There is more area to the right of Z minima than to the left.

Figure 9:
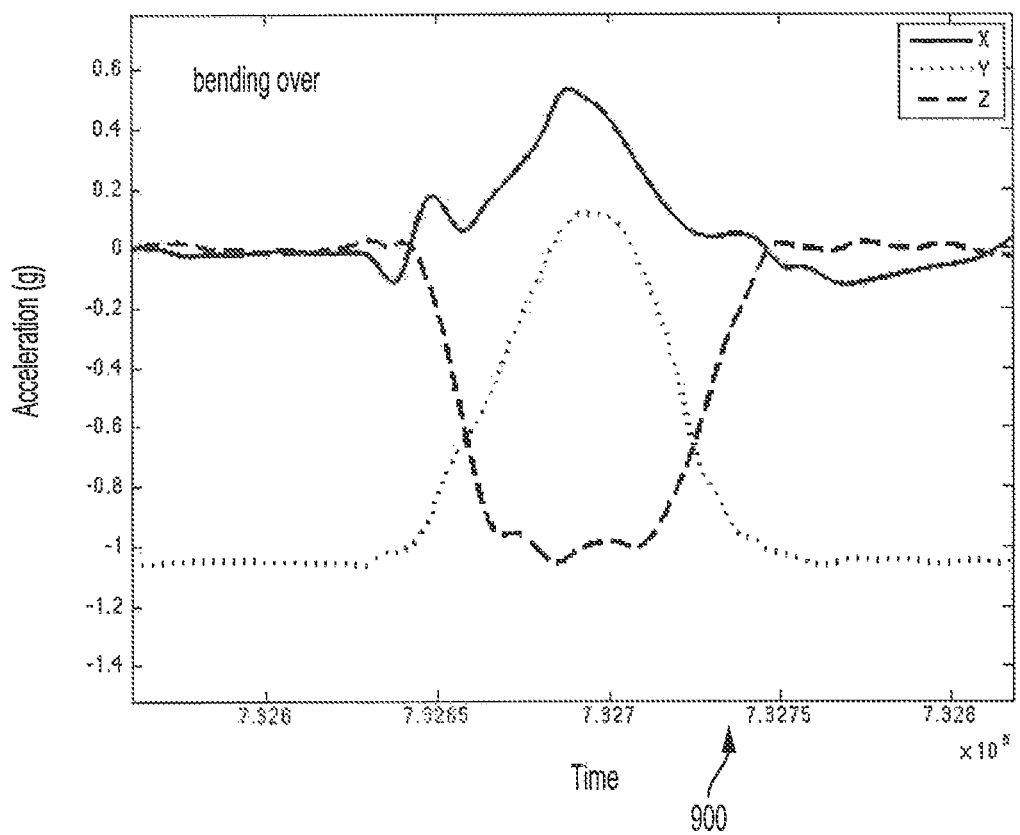
FIG. 9 illustrates a graph showing body transitions in accordance with an embodiment.

FIG. 9 illustrates a graph 900 showing body transitions in accordance with an embodiment. With regard to bending over, the graph looks similar to sit/stand transitions, but much larger Y maxima and longer duration. The maxima is larger, the minima is smaller.

Transition Detection

Figure 10:
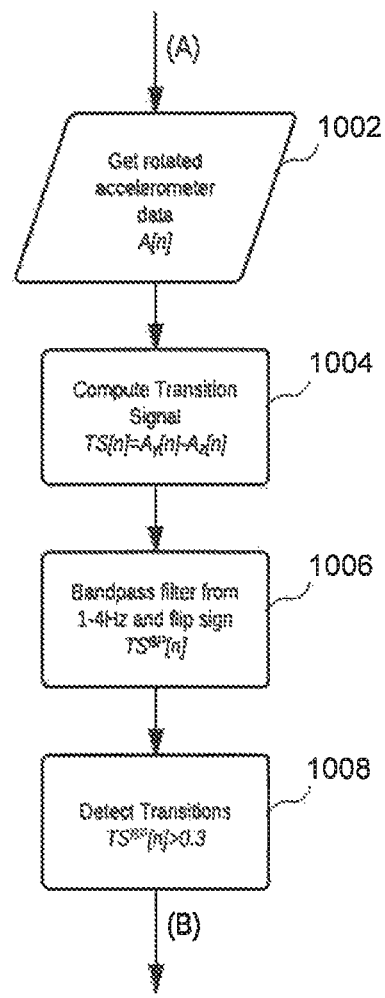
FIG. 10 illustrates a method for detecting transitions in accordance with an embodiment.
Figure 11:
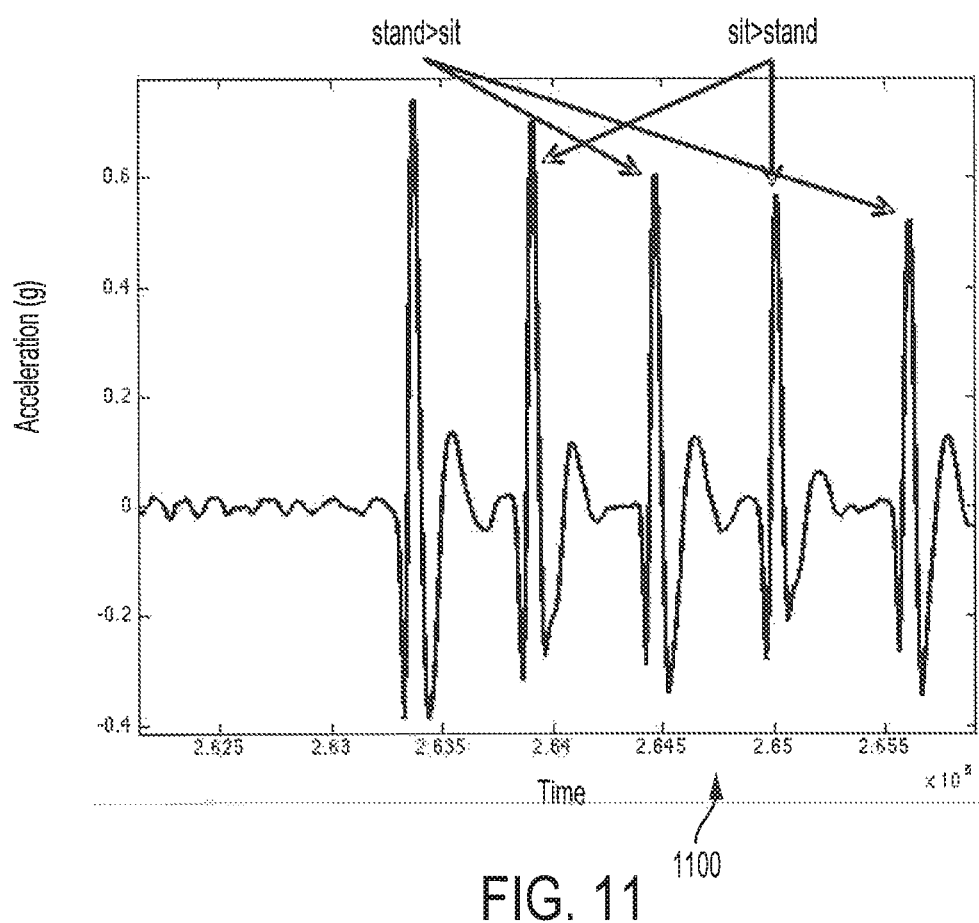
FIG. 11 illustrates a graph showing transition detection in accordance with an embodiment.

FIG. 10 illustrates a method for detecting transitions in accordance with an embodiment. Referring to FIGS. 3 and 10, the flow chart of FIG. 10 corresponds to step 308 (Detect Transitions) of the flow chart of FIG. 3. Referring to FIG. 10, the wireless sensor device 100 obtains the calibrated/rotated acceleration data, via step 1002. The wireless sensor device 100 then computes transition signals, via step 1004. The transition signal is the acceleration on the Y-axis minus the acceleration on the Z-axis. The wireless sensor device 100 then applies a band-pass filter, via step 1006. The wireless sensor device 100 then detects transitions, via step 1008. If the transition signal exceeds a threshold, a transition is detected. FIG. 11 illustrates a graph showing transition detection 1100 in accordance with an embodiment.

Transition Classification

Figure 12:
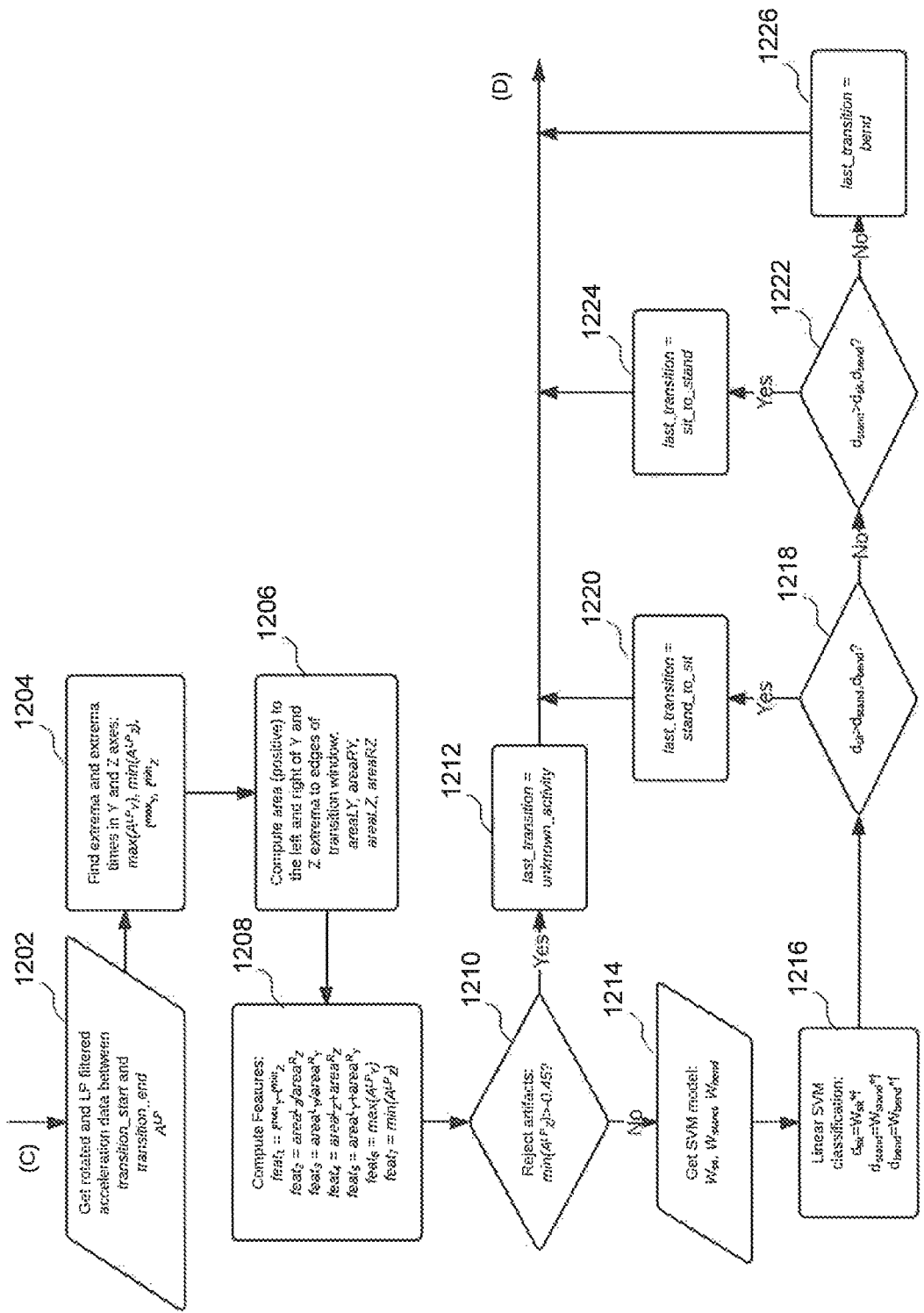
FIG. 12 illustrates a method for classifying transitions in accordance with an embodiment.

FIG. 12 illustrates a method for classifying transitions in accordance with an embodiment. Referring to FIGS. 3 and 12 the flow chart of FIG. 12 corresponds to step 322 (Classify Transition) of the flow chart of FIG. 3. As described in more detail below, the transitions detected include stand-to-sit, sit-to-stand, and bending over.

Referring to FIG. 12, the wireless sensor device 100 obtains rotated and low-pass filtered acceleration data, $A^{LP}$, between transition_start and transition_end, via step 1202.

The wireless sensor device 100 then finds extrema values and extrema times in Y and Z axes: max ($A^{LP}_X$), min ($A^{LP}_Z$), $t^{max}_Y$, $t^{min}_Z$, via step 1204. The wireless sensor device 100 then computes area (positive) to the left and right of Y and Z extrema to edges of transition window: $area^L_Y$, $area^R_Y$, $area^L_Z$, $area^L_Z$, via step 1206.

The wireless sensor device 100 then computes features for each detected transition and put the features into a feature vector, f, via step 1208. In some embodiments, the features may also include any combination of the following features: time of the Y-max minus the time of the Z-min, ratio of areas to the left and right of Z-min, ratio of areas to the left and right of Y-min, the total area of the Z-min, the total area of the Y-max, the value of the Y-max, and the value of the Z-min.

The wireless sensor device 100 then rejects artifacts that may look like posture transitions, via step 1210. If the minima in the Z-axis is less than a threshold (e.g. −0.45), the transition in question is considered an artifact. If this is true, the wireless sensor device 100 stores the last transition as unknown, via step 1212. If the minima in the Z-axis is not less than the threshold, the wireless sensor device 100 obtains a classification model, via step 1214. In one embodiment, this classifier may be a linear SVM consisting of three weight vectors: $W_{sit}$, $W_{stand}$, $W_{bend}$.

The wireless sensor device 100 then uses the classification model to classify the transition type, via step 1216. In some embodiments, the wireless sensor device 100 uses support vector machines, SVM. In some embodiments, the linear SVM may be a dot product between the feature vector, f, and a weight vector ($W_{sit}$, $W_{stand}$, $W_{bend}$) for each of the classes (sit, stand, bend) resulting in three discriminant values, $d_{sit}$, $d_{stand}$, $d_{bend}$. In some embodiments, the largest dot product ($d_{sit}$, $d_{stand}$, $d_{bend}$) determines the classification of that transition. In some embodiments, $d_{sit}=W_{sit}*f$, $d_{stand}=W_{stand}*f$, and $d_{bend}=W_{bend}*f$.

The wireless sensor device 100 determines if $d_{sit}>d_{stand}$, $d_{bend}$, via step 1218. If so, the wireless sensor device 100 stores the last transition as stand-to-sit, and stores the time of the last transition, via step 1220. If not, the wireless sensor device 100 determines if $d_{stand}>d_{sit}$, $d_{bend}$, via step 1222. If so, the wireless sensor device 100 stores the last transition as sit-to-stand, and stores the time of the last transition, via step 1224. If not, the wireless sensor device 100 stores the last transition as bending over, and stores the time of the last transition, via step 1226.

Transition Feature Explanation

Figure 13:
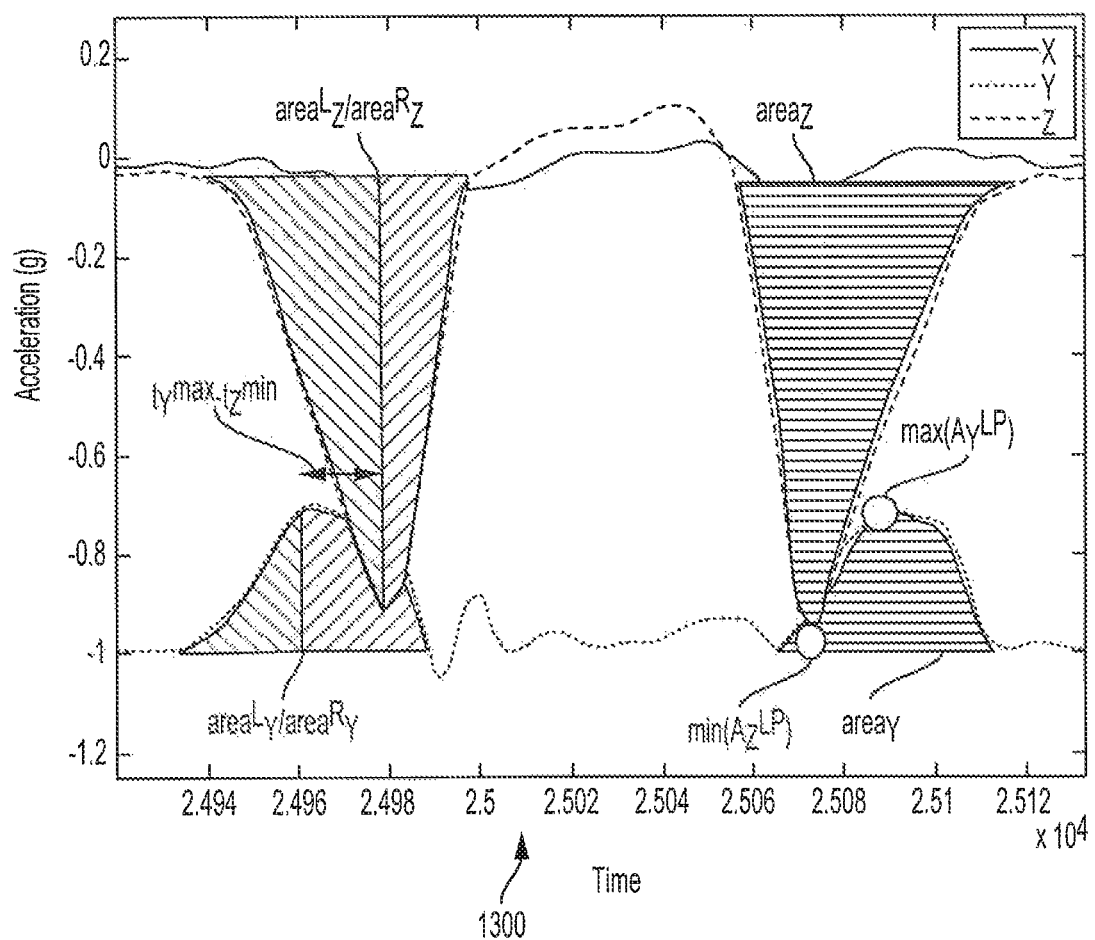
FIG. 13 illustrates a graph showing transition features and transition detection in accordance with an embodiment.

FIG. 13 illustrates a graph 1300 showing transition features and transition detection in accordance with an embodiment. Shown are seven features computed for each transition, where a classifier uses the features to distinguish between sit>stand, stand>sit, and bending.

The first feature is the time between the y max and the z min, which is time of y-max minus time of z-min ($t_Y^{max} - t_Z^{min}$). This value can be a positive or negative value. In some embodiments, negative indicates stand-to-sit, and positive indicates sit-to-stand.

The second feature is the ratio of area to left and right of z-min ($area^L_Z/area^R_Z$). This is an area of the left of z divided by area of the right of z. The third feature is the ratio of area to left and right of y-min ($area^L_Y/area^R_Y$). The fourth feature is the total area of z-min ($area_Z$). The fifth feature is the total area of y-max ($area_Y$). The sixth feature is the value of y-max, ($max(A_Y^{LP})$). The seventh feature is value of z-min, ($min(A_Z^{LP})$).

The number of features may vary and the particular number will depend on the particular implementation.

Linear Classification of Features

Figure 14:
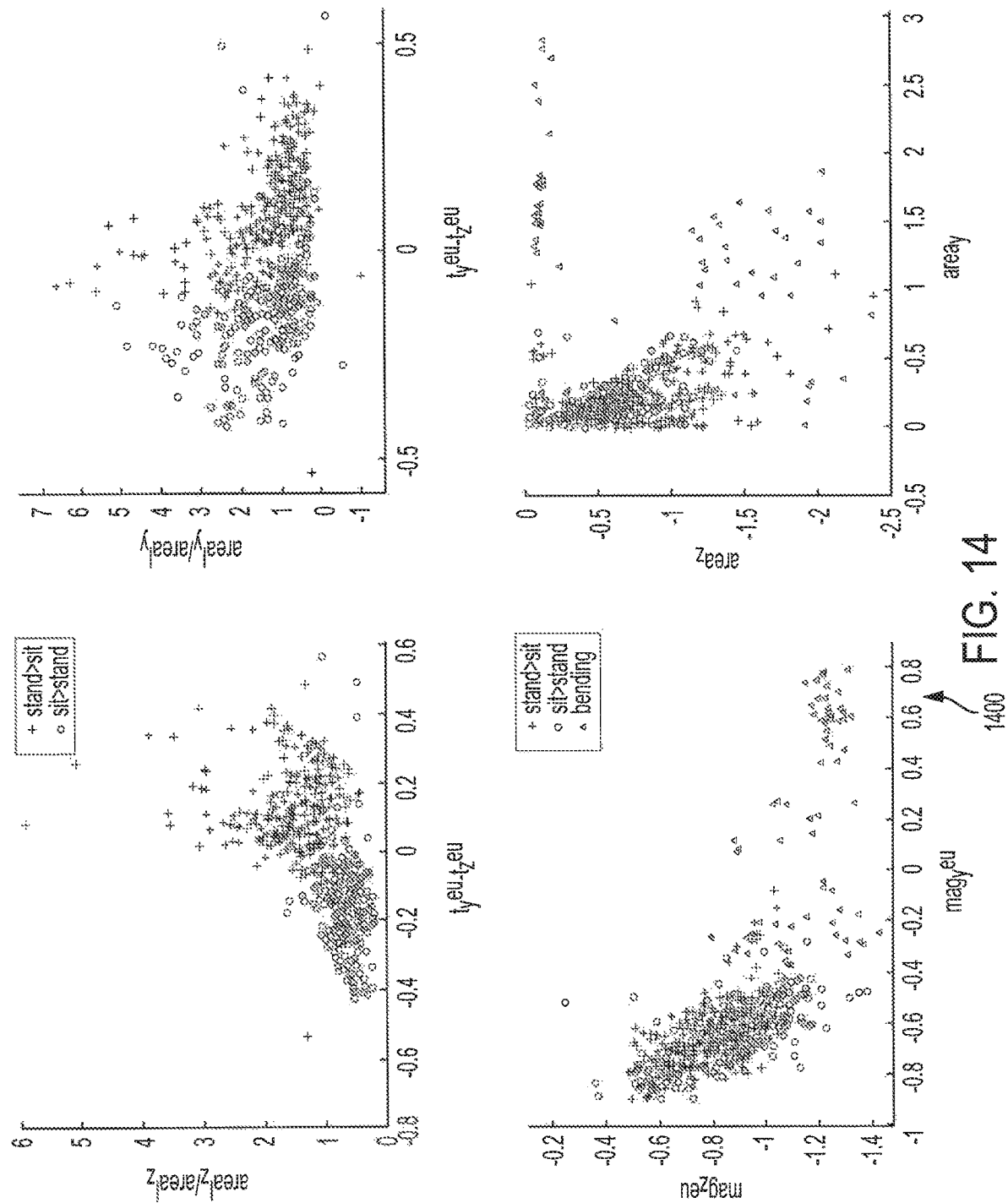
FIG. 14 illustrates a graph showing a linear classification of features in accordance with an embodiment.

FIG. 14 illustrates a graph 1400 showing a linear classification of features in accordance with an embodiment. As shown, each point in these plots is a single transition, and the axes are the features plotted against each other. Also, sitting (circles) and standing (crosses) are clearly separable by a line. Bending (triangles) are also separable. The linear classifier finds a linear boundary to separate these classes.

Rest Classification

Figure 15:
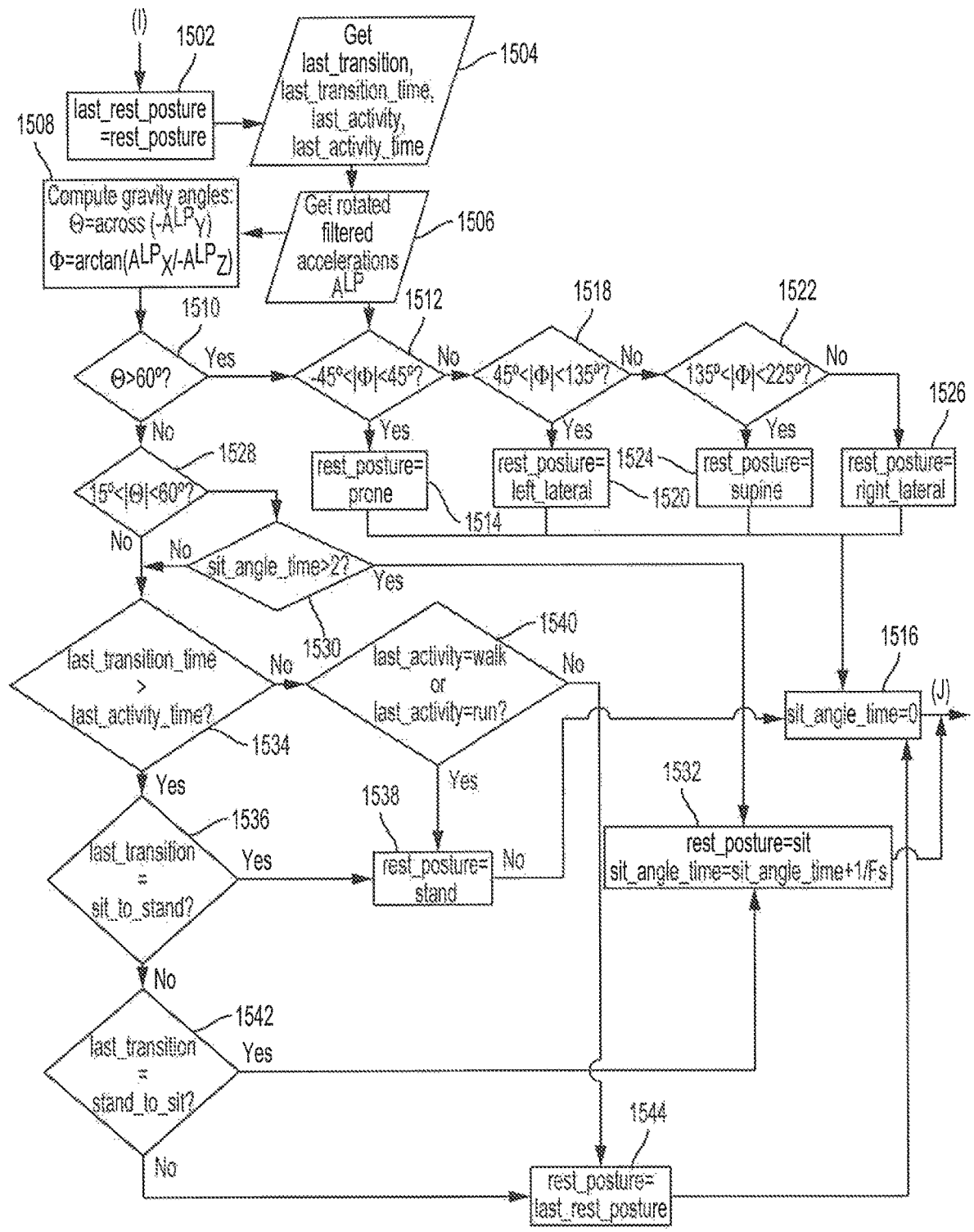
FIG. 15 illustrates a method for classifying rest in accordance with an embodiment.

FIG. 15 illustrates a method for classifying rest in accordance with an embodiment. Referring to FIGS. 3 and 15 the flow chart of FIG. 10 corresponds to step 330 (Classify Rest) of the flow chart of FIG. 3. In general, while no activity is going on, the wireless sensor device 100 uses body angle, last transition, and last activity to classify sit, stand, or lying.

Referring to FIG. 15, the wireless sensor device 100 stores the last rest posture as the current rest posture, via step 1502. The wireless sensor device 100 then obtains the last transition, the last transition time, the last activity, and the last activity time, via step 1504. The wireless sensor device 100 obtains rotated filtered accelerations, via step 1506.

The wireless sensor device 100 computes gravity angles θ and φ, via step 1508. In some embodiments, θ=arccos(−$A^{LP}_Y$), and φ=arctan($A^{LP}_X/-A^{LP}_Z$).

The wireless sensor device 100 determines if θ>60°, via step 1510.

If θ>60°, the wireless sensor device 100 determines that the body is lying down. In some embodiments, theta θ is a vertical angle (e.g., how upright the body is), and phi φ is an angle used when the body you are lying down and rotated. In some embodiments, the wireless sensor device 100 uses φ to determine the lying subposture, phi φ may be viewed as 90 degree quadrants (e.g., prone, left lateral, supine, or right lateral). If −45°<|φ|<45°, the wireless sensor device 100 determines that the rest posture is prone (lying on stomach), via step 1514. The wireless sensor device 100 then resets the sit angle time to 0, via step 1516.

If not −45°<|φ|<45°, the wireless sensor device 100 determines if 45°<|φ|<135°, via step 1518. If 45°<|φ|<135°, the wireless sensor device 100 determines that the rest posture is left lateral, via step 1520, and then resets the sit angle time to 0, via step 1516.

If not 45°<|φ|<135°, the wireless sensor device 100 determines if 135°<|φ|<225°, via step 1522. If 135°<|φ|<225°, the wireless sensor device 100 determines that the rest posture is supine (lying on back), via step 1524, and then resets the sit angle time to 0, via step 1516.

If not 135°<|φ|<225°, the wireless sensor device 100 rest posture is right lateral, via step 1526, and then resets the sit angle time to 0, via step 1516.

Referring again to step 1510, if θ is not >60°, the wireless sensor device 100 determines if 15°<|φ|<60°, via step 1528. In some embodiments, when the body is 15°<|φ|<60°, the wireless sensor device 100 determines the body to be sitting.

If 15°<|θ|<60°, the wireless sensor device 100 determines if the sit angle time >2, via step 1530, and if so, the rest posture is classified as sitting. The sit angle time is then incremented by the sampling time 1/Fs, via step 1532. If not, the wireless sensor device 100 determines if last transition time>last activity time, via step 1534. Note that if the body is inclined at an angle that is too severe for standing, the wireless sensor device 100 classifies the body as sitting (15°<θ<60°). Otherwise, the body is in an ambiguous zone. Also, if last transition stand-to-sit, then the wireless sensor device 100 determines that the body is sitting.

Note that if the body is 15°<|θ|<60°, the wireless sensor device 100 counts the time that the body is in that angle range. If it is in that range for at least 2 seconds, then the wireless sensor device 100 determines that the body is sitting. If it is less than 2 seconds, the wireless sensor device 100 performs further analysis to determine sitting or standing postures. In one embodiment, the time is incremented while in that angle, where the time needs to be at least two seconds to detect sitting. If the body transitions to standing, the wireless sensor device 100 resets the sit angle time to zero, at step 1532.

If last transition time>last activity time, meaning the last transition occurred more recently than the last activity, the wireless sensor device 100 determines if the last transition=sit-to-stand, via step 1536. If so, the wireless sensor device 100 determines that the rest posture=stand, via step 1538, and then sets the sit angle time 0, via step 1516.

Referring again to step 1534, if the last activity time was greater than the last transition time, meaning the last activity occurred more recently than the last transition, the wireless sensor device 100 determines if the last activity=walk or the last activity=run, via step 1540. If the last activity=walk or the last activity=run, the wireless sensor device 100 determines that the rest posture=stand, via step 1538, and then sets the sit angle time=0, via step 1516. If not, the wireless sensor device 100 determines that the rest posture=the last rest posture, or keep the rest posture unchanged, via step 1544, and then sets the sit angle=0, via step 1516.

Referring again to step 1536, if the last transition is not=sit-to-stand, the wireless sensor device 100 determines if the last transition=stand-to-sit, via step 1542.

If the last transition=stand-to-sit, the wireless sensor device 100 determines that the rest posture=sit and that the sit angle time=sit angle time+1/Fs, via step 1532. If not, the wireless sensor device 100 determines that the rest posture=the last rest posture, via step 1544, and then sets the sit angle=0, via step 1516.

Estimating Severity of Orthopnea

Figure 16:
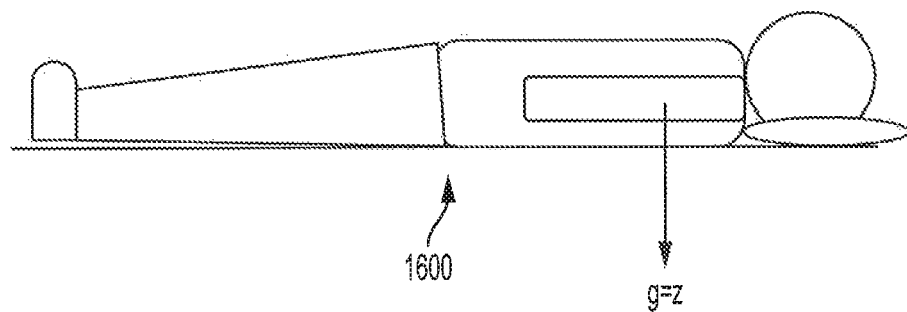
FIG. 16 illustrates an example supine position of a body in accordance with an embodiment.

FIG. 16 illustrates an example supine position 1600 of a body in accordance with an embodiment. In some scenarios patients with orthopnea have shortness of breath while supine (lying on back). Patients often use pillows to provide inclined sleeping position. Clinicians often ask how many pillows a patient uses to judge severity (the more pillows, the more severe).

Figure 17:
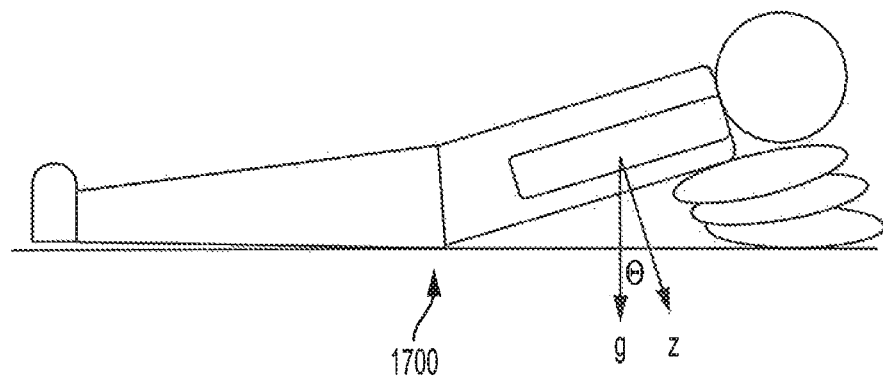
FIG. 17 illustrates an example supine position of a body in accordance with an embodiment.

FIG. 17 illustrates an example supine position 1700 of a body in accordance with an embodiment. As shown, the body is held up by more pillows. In one embodiment, theta θ may be used for quantification of incline during sleep. A lying posture (e.g., supine) can be detected using theta greater than 60 (θ>60°). Then looking at the specific angle, the wireless sensor device 100 take 90° minus the theta and looks at the angle at which they are inclined and then estimates a particular range of angles that corresponds to one or two or three or four pillows. In some embodiments, the following angles may be determined: supine position (135°<φ<225°); and Incline angle=90°−θ, where 0°<angle$_{incline}$<5°~1 pillow, 5°<angle$_{incline}$<15°~2 pillows, 15°<angle$_{incline}$<25°~3 pillows, 25°<angle$_{incline}$<35°~4 pillows.

Robust Step Counting

Various every day activates such as moving around while sitting on a chair may register patterns on the MEMs device that are close to that of walking. One distinguishing feature between these activities and walking is generally regular intervals between the steps during an actual walk (or a run) and irregular, random intervals between other activities. This distinction is utilized to prevent sporadic movements from being counted as steps.

In some embodiments, a filter uses a buffer of length N_STEP to store the interval between the last N_STEP+1 steps. Every time there is a new step candidate, time interval from the last step candidate is calculated. Buffer is updated and the step candidate is counted as a real step only if the last N_STEP+1 steps occurred within T_MAX_STEP of the following step. The wireless sensor device 100 can compute this buffer of step intervals, and then compute kurtosis.

Rejecting Fake Steps During Non-Walking Activities

Movements caused by other activities like driving (i.e. bumps in the road) could be mistaken for actual steps. These car movements happen more irregularly than steps during walking. Distribution of the step intervals during a walk is close to a uniform distribution while the distribution of the car movements is more spiky. A combination of the Kurtosis of the step intervals and activity level are used to determine whether step candidates are genuine steps or movements caused by driving.

Also, walking causes a side-to-side sway that happens at half the frequency of the steps that other activities do not show. In some embodiments, the wireless sensor device 100 determines the average frequency of minima in the vertical axis, mean(freq$_Y$) and the average frequency of minima AND maxima in the left-right axis, mean(freq$_X$). The ratio mean(freq$_Y$)/mean(freq$_X$) should be close to 1 for walking and running.

In some embodiments, the wireless sensor device 100 rejects fake steps. Fake steps could be caused by things like driving, or taking a step without walking. The distribution of the step intervals is very regular during actual walking. So if plotted in a histogram, intervals would be a very spiky for actual walking, because most of the steps have about the same interval. If the person is driving, the intervals would be spread out. Kurtosis is a statistical measure that measures the spikiness of the distribution. The wireless sensor device 100 can use that to distinguish between real steps and fake steps. The wireless sensor device 100 can also analyze side to side sway that occurs in walking, which happens at half the frequency of the up and down step motion. The wireless sensor device 100 determines this ratio of the frequency in the wide y direction.

Overall Step Counting Algorithm

Figure 18:
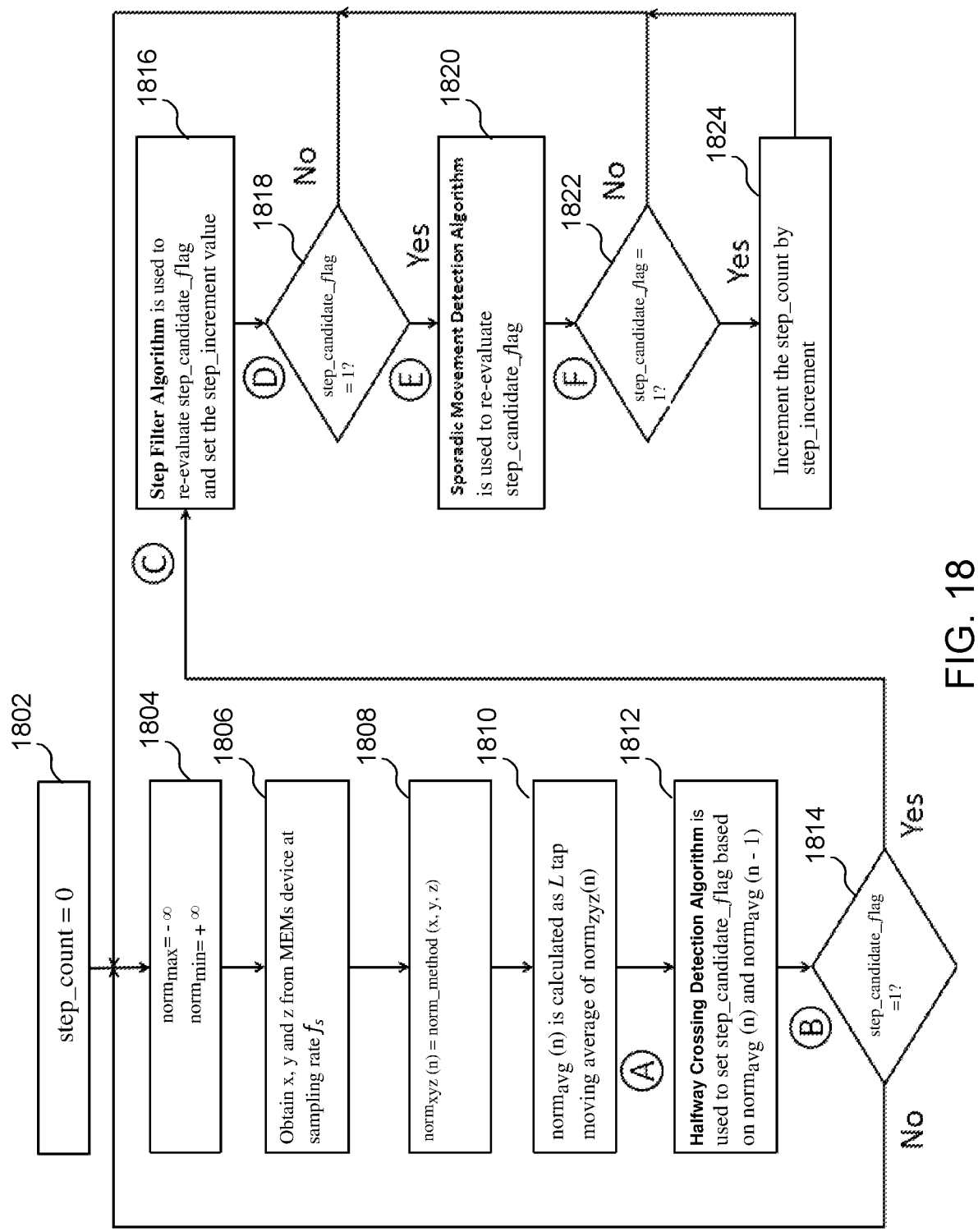
FIG. 18 illustrates a method for a step counting algorithm in accordance with an embodiment.

FIG. 18 illustrates a method for a step counting algorithm in accordance with an embodiment. The wireless sensor device 100 initializes the step count to 0, via step 1802. The wireless sensor device 100 normalizes the steps, via step 1804. The wireless sensor device 100 obtains x, y, z from MEMs device at sampling rate fs, via step 1806. The wireless sensor device 100 then normalizes x, y, and z, via step 1808. The wireless sensor device 100 determines an average, via step 1810.

The wireless sensor device 100 applies a halfway crossing detection algorithm, via step 1812. In one embodiment, the wireless sensor device 100 detects steps by determining when the acceleration crosses half way between the min and max. At that point, the step might be a step candidate.

The wireless sensor device 100 then determines if the step_candidate_flag=1, via step 1814. If not, the wireless sensor device 100 returns to step 1804. If the step_candidate_flag=1, the wireless sensor device 100 applies a step filter algorithm, via step 1816. The wireless sensor device 100 uses the step filter algorithm to determine whether a step an actual step and to filter out possible fake steps.

The wireless sensor device 100 then determines if the step_candidate_flag=1, via step 1818. If not, the wireless sensor device 100 returns to step 1804. If the step_candidate_flag=1, the wireless sensor device 100 applies a sporadic movement detection algorithm, via step 1820.

The wireless sensor device 100 then determines if the step_candidate_flag=1, via step 1822. If not, wireless sensor device 100 returns to step 1804. If the step_candidate_flag=1, the increments the step count, via step 1824.

Detection of a step is done by finding the local min and the local max. The max has to be above some threshold, the min has to be below some threshold, and whenever the accelerations cross zero, when both of those things are detected, a step is counted at that zero-crossing.

Figure 19:
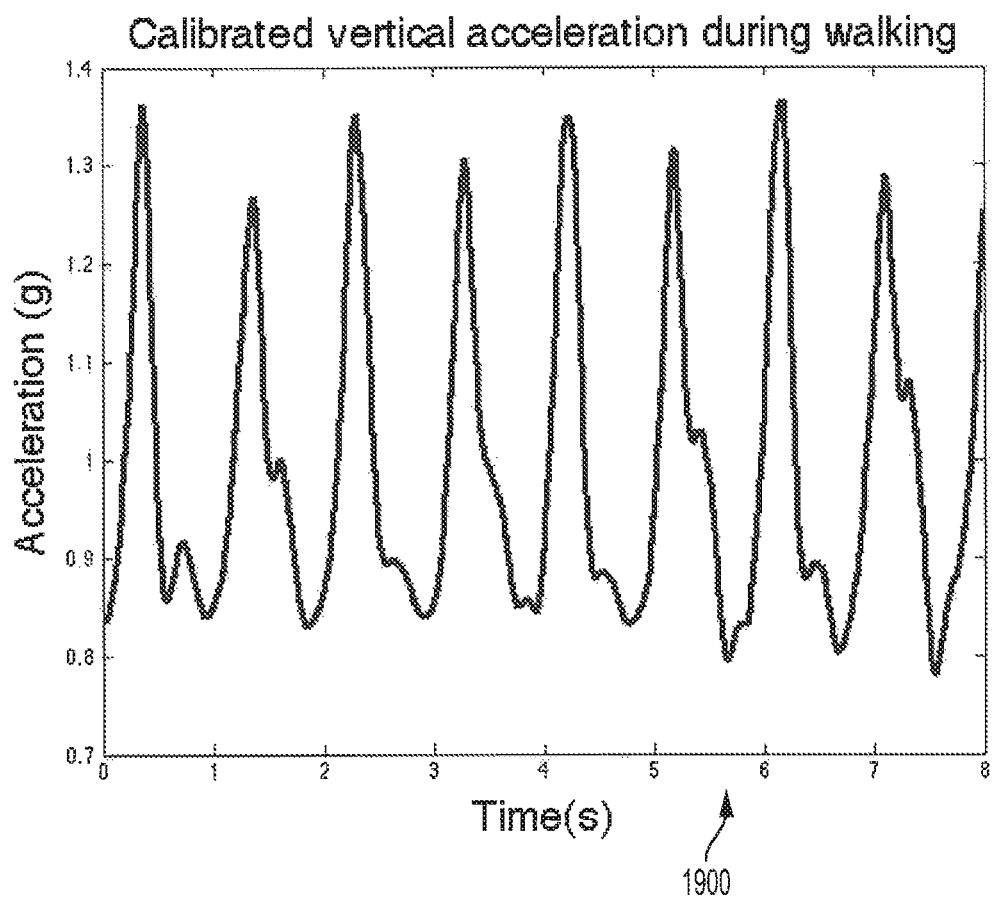
FIG. 19 illustrates a graph showing calibrated vertical acceleration during walking in accordance with an embodiment.
Figure 20:
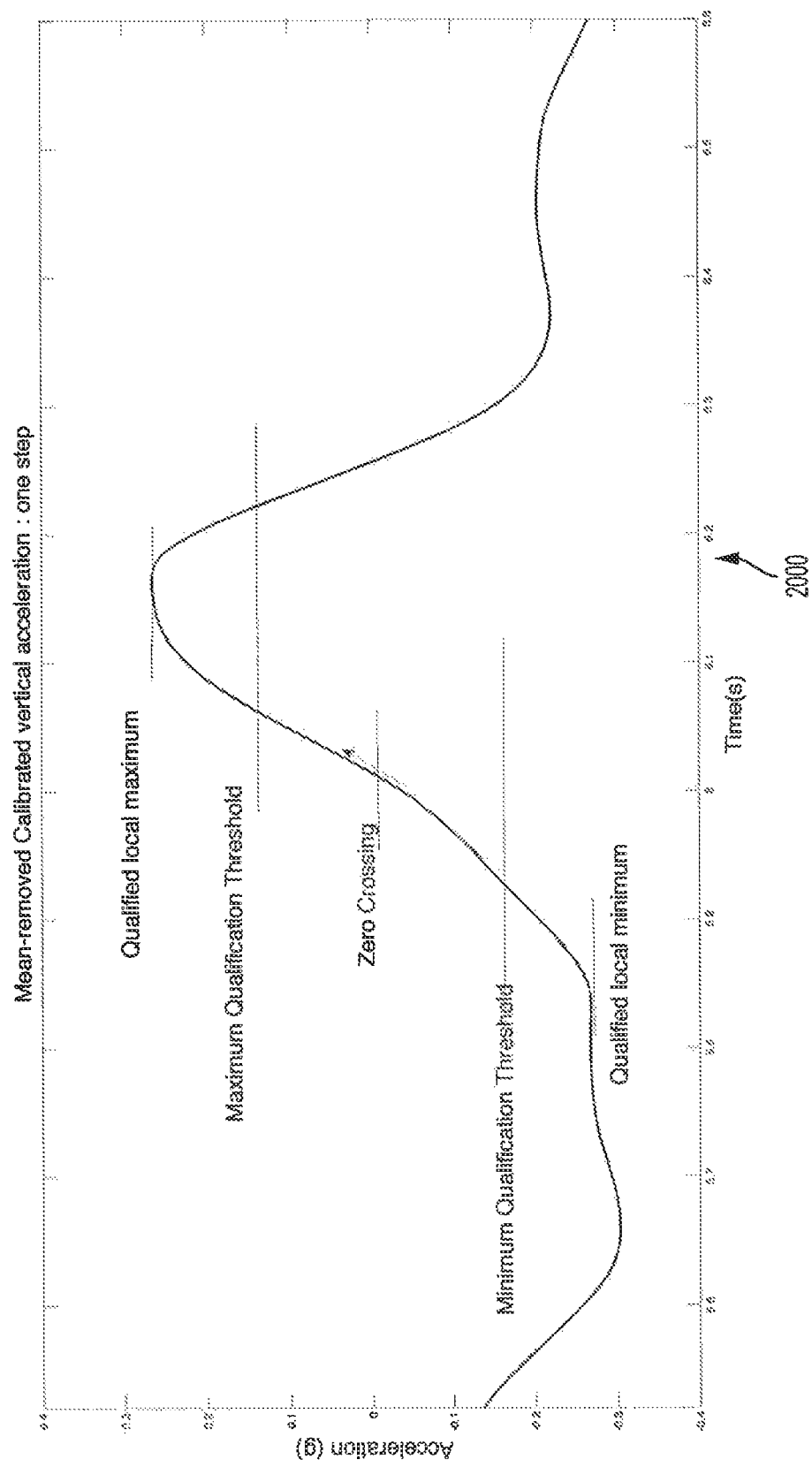
FIG. 20 illustrates a graph showing a mean-removed calibrated vertical acceleration (one step) in accordance with an embodiment.

FIG. 19 illustrates a graph 1900 showing calibrated vertical acceleration during walking in accordance with an embodiment. FIG. 20 illustrates a graph 2000 showing a mean-removed calibrated vertical acceleration (one step) in accordance with an embodiment.

Figure 21:
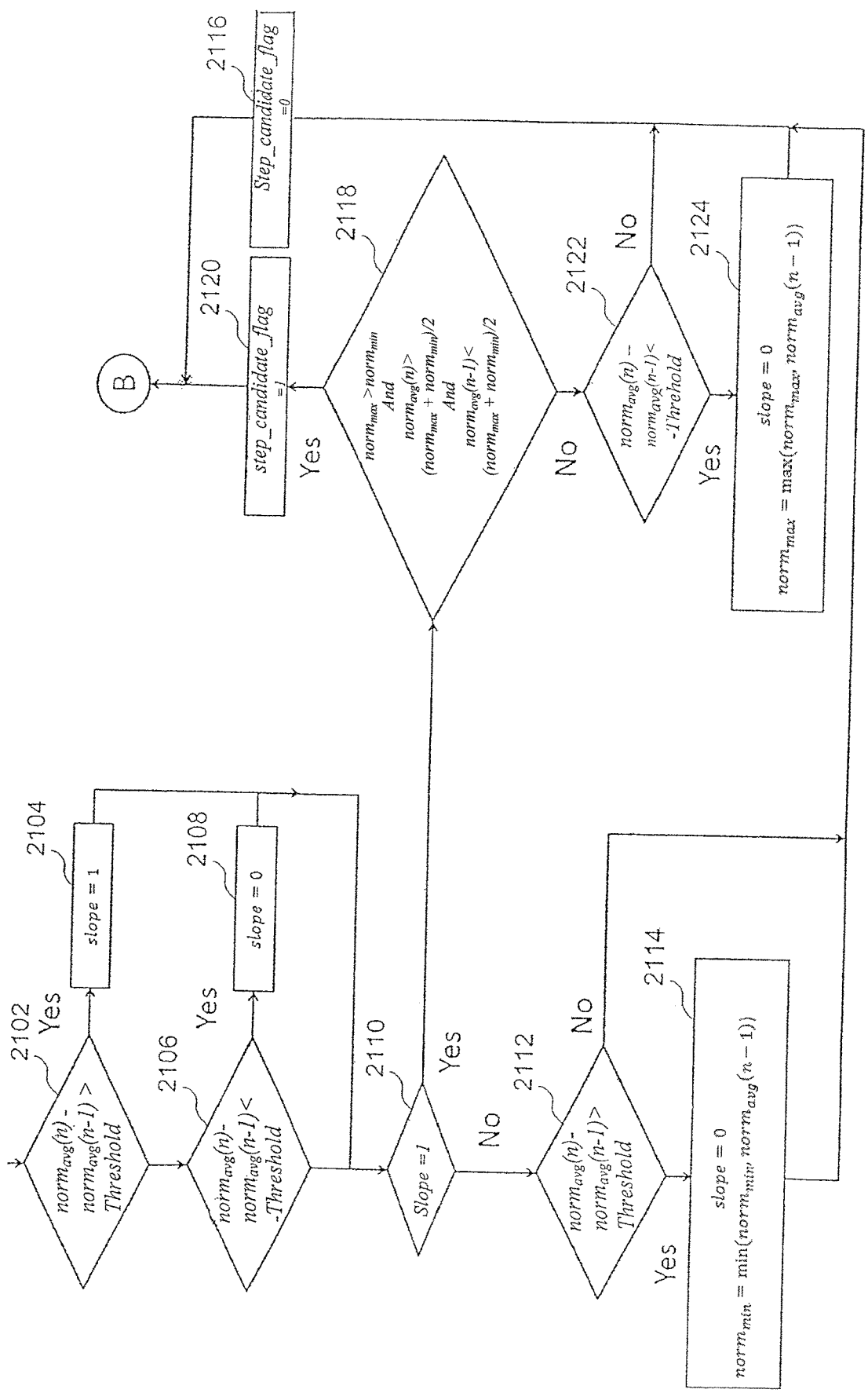
FIG. 21 illustrates a method for a step picking algorithm in accordance with an embodiment.

FIG. 21 illustrates a method for a step picking algorithm in accordance with an embodiment. Referring to FIGS. 18 and 21, the flow chart of FIG. 21 is an input to step 1814 of the flow chart of FIG. 18. Referring to FIG. 21, the wireless sensor device 100 determines if $norm_{avg}(n)-norm_{avg}(n-1)>threshold$, via step 2102. If yes, the wireless sensor device 100 sets the slope=1, via step 2104. If no, the wireless sensor device 100 determines if $norm_{avg}(n)-norm_{avg}(n-1)<-threshold$, via step 2106. If yes, the wireless sensor device 100 sets the slope=0, via step 2108. If no, the wireless sensor device 100 determines of the slope=1, via step 2110. If no, the wireless sensor device 100 determines if the normalized step is greater than a threshold, via step 2112. If yes, the wireless sensor device 100 sets the slope=0, where $norm_{min}=min(norm_{min}, norm_{avg}(n-1)$, via step 2114, and then sets the step_candidate_flag=0, via step 2116

Referring again to step 2110, if the slope=1, the wireless sensor device 100 determines if $norm_{max}>norm_{min}$, and $norm_{avg}(n)>(norm_{max}+norm_{min})/2$, and $norm_{avg}(n-1)<(norm_{max}+norm_{mm})/2$, via step 2218. If yes, the wireless sensor device 100 sets step_candidate_flag=1, via step 2220. If no, the wireless sensor device 100 determines if $norm_{avg}(n)-norm_{avg}(n-1)<-threshold$, via step 2222, and then sets the step_candidate_flag=0, via step 2216.

If $norm_{avg}(n)-norm_{avg}(n-1)<-threshold$, the wireless sensor device 100 sets the slope=0, where $norm_{max}=min(norm_{max}, norm_{avg}(n-1)$, via step 2224, and then sets the step_candidate_flag=0, via step 2216.

Figure 22:
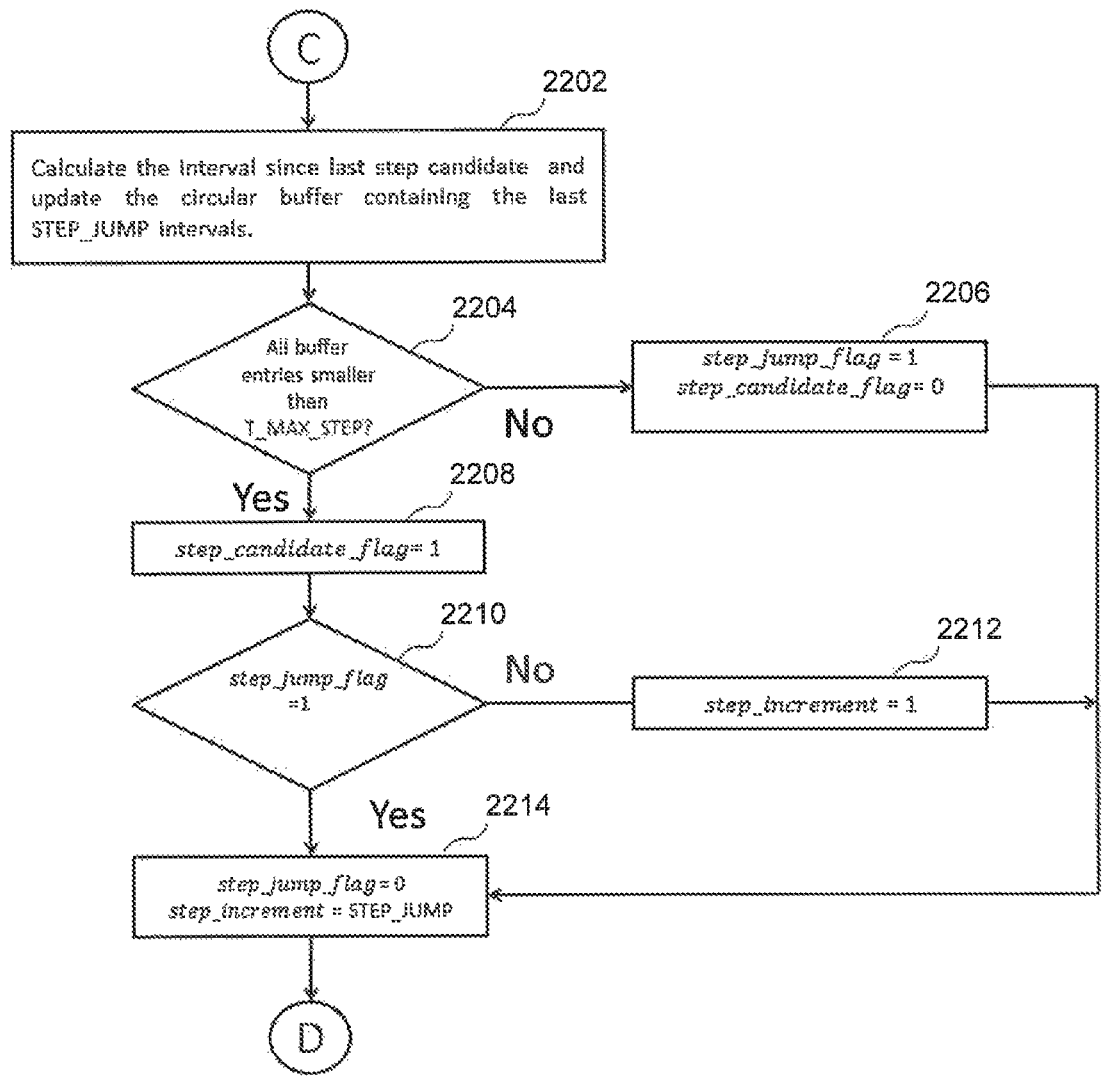
FIG. 22 illustrates a method for a step filter algorithm in accordance with an embodiment.

FIG. 22 illustrates a method for a step filter algorithm in accordance with an embodiment. Referring to FIGS. 18 and 22, the flow chart of FIG. 22 corresponds to step 1816 (Filter Algorithm) of the flow chart of FIG. 18. As described in more detail below, the step filter algorithm calculates the interval since the last step. If all the step intervals are less than a predetermined threshold, it is a candidate. Referring to FIG. 22, the wireless sensor device 100 calculates the interval since the last step candidate and updates the circular buffer containing the last step jump intervals, via step 2202.

The wireless sensor device 100 determines if all buffer entries are smaller than T_MAX_STEP, via step 2204. If not, the wireless sensor device 100 sets the step_jump_flag=1 and step_candidate_flag=0, via step 2206. If so, the wireless sensor device 100 sets the step_candidate_flag=1, via step 2208.

The wireless sensor device 100 then determines if the step_jump_flag=1, via step 2210. If not, the wireless sensor device 100 sets the step_increment=1, via step 2212. If so, the wireless sensor device 100 sets the step_jump_flag=0 and the step_increment=STEP_JUMP, via step 2214.

Figure 23:
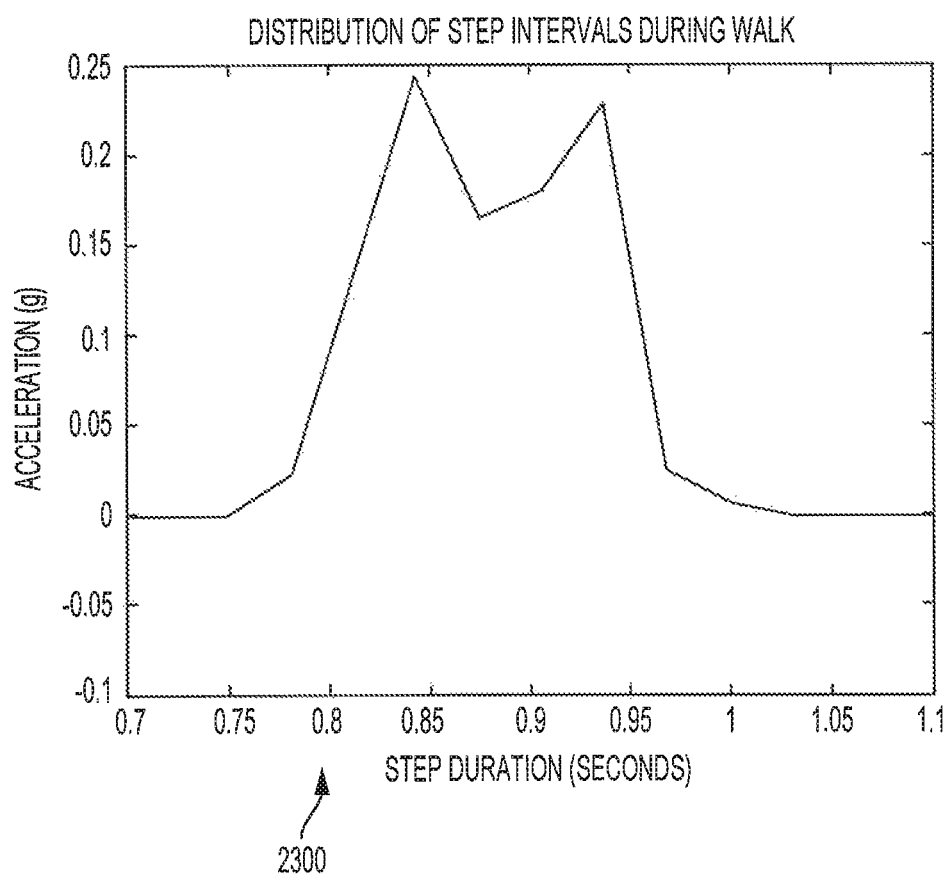
FIG. 23 illustrates a graph showing a distribution of step intervals during walking in accordance with an embodiment.
Figure 24:
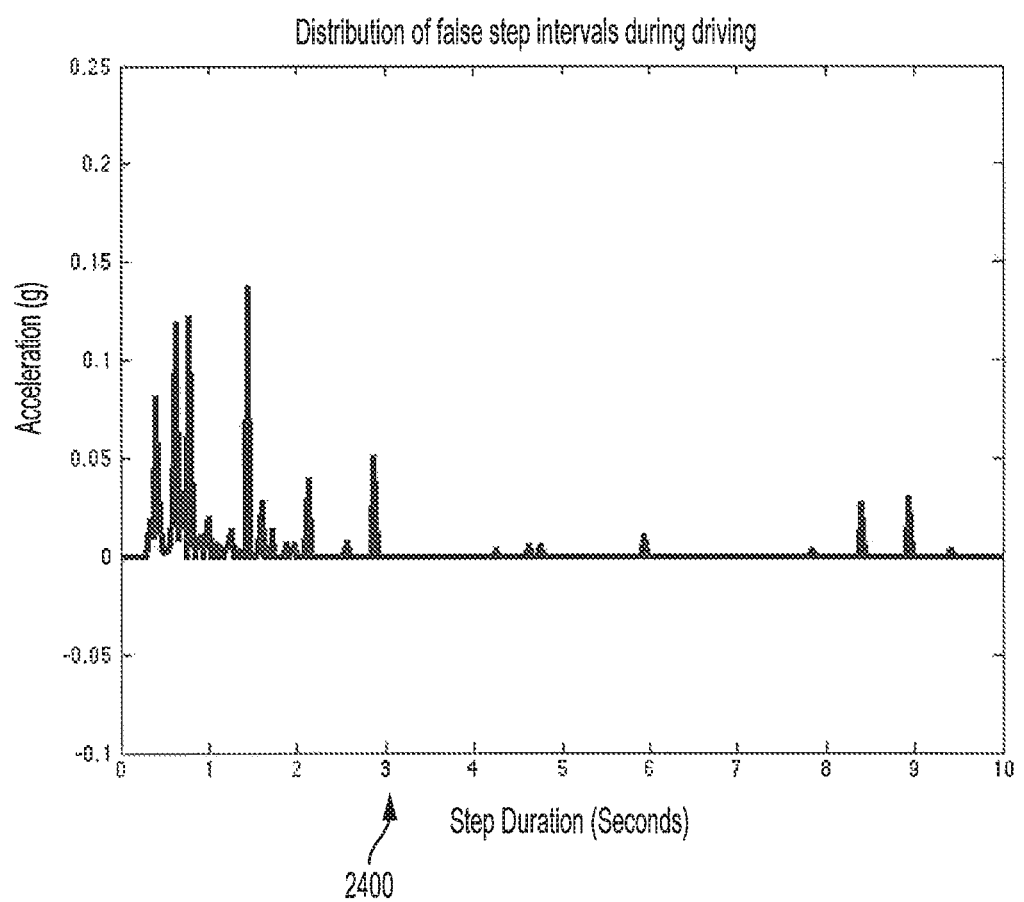
FIG. 24 illustrates a graph showing a distribution of false step intervals during driving in accordance with an embodiment.
Figure 25:
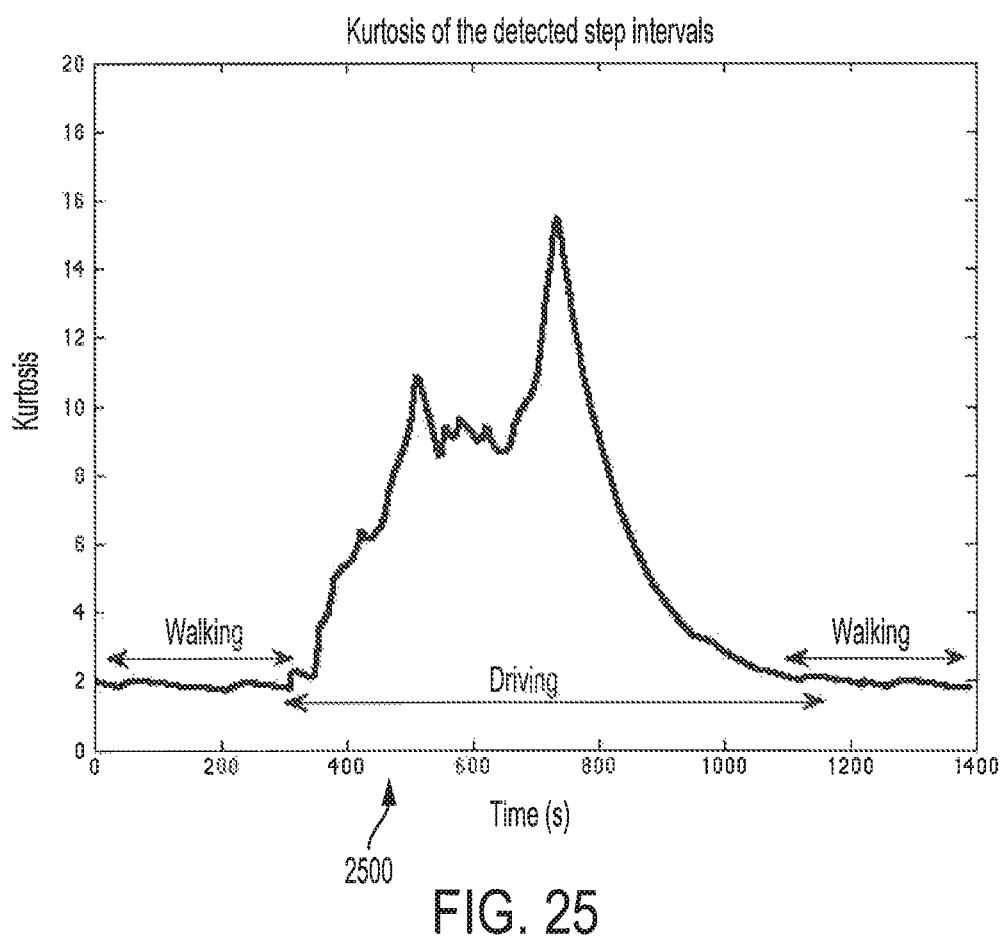
FIG. 25 illustrates a graph showing Kurtosis of the detected step intervals in accordance with an embodiment.

FIG. 23 illustrates a graph 2300 showing a distribution of step intervals during walking in accordance with an embodiment. FIG. 24 illustrates a graph 2400 showing a distribution of false step intervals during driving in accordance with an embodiment. FIG. 25 illustrates a graph 2500 showing Kurtosis of the detected step intervals in accordance with an embodiment.

Figure 26:
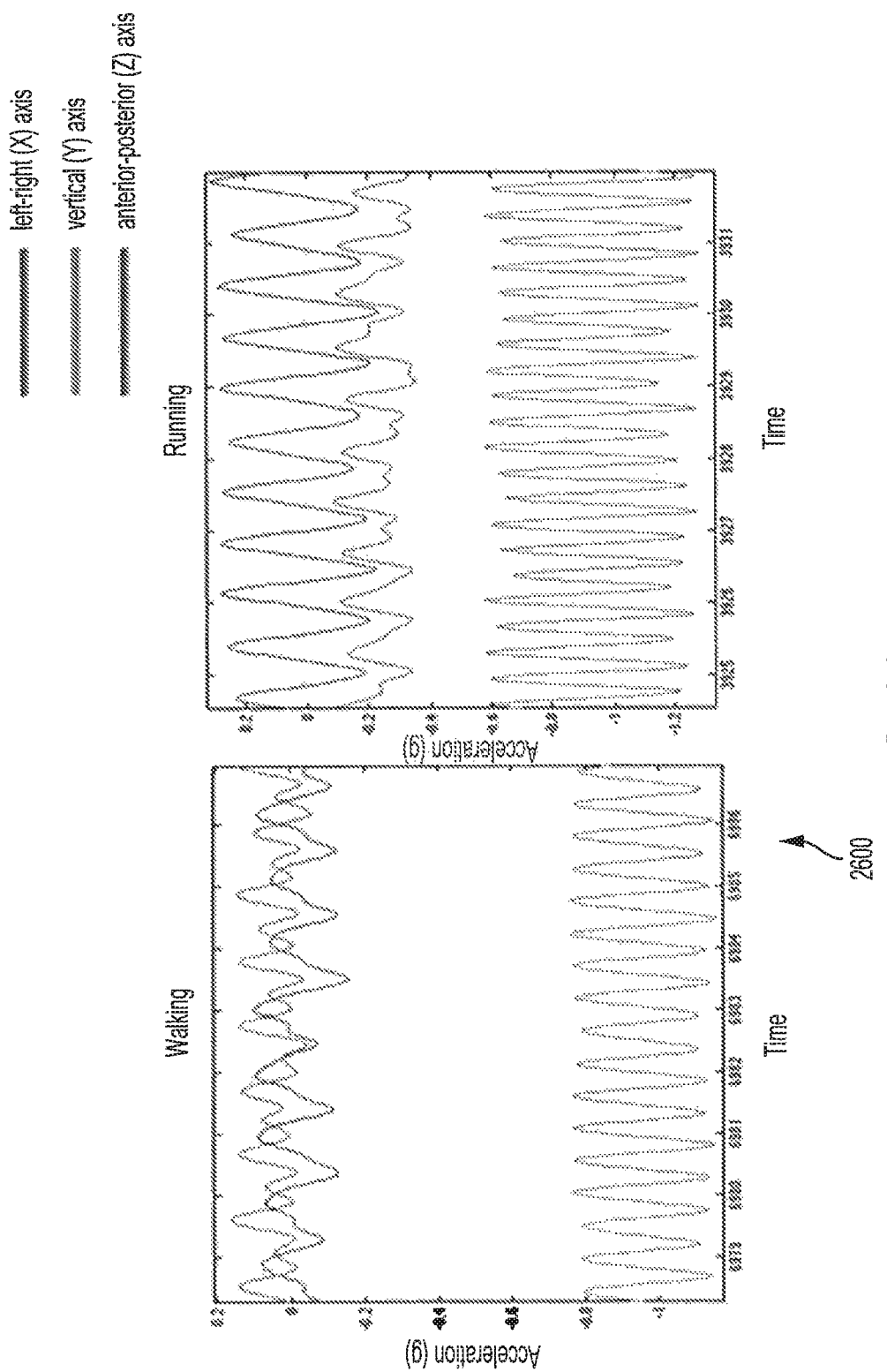
FIG. 26 illustrates a graph showing side-to-side sway during walking/running in accordance with an embodiment.

FIG. 26 illustrates a graph 2600 showing side-to-side sway during walking/running in accordance with an embodiment. As shown, during walking and running, the frequency of the left to right is half of the frequency of the vertical. As such, if each of the minima is selected for the vertical accelerations, the mean frequency of the vertical minima can be computed as 1/mean(time between minima). If the min and max are selected for the left to right accelerations, the mean frequency of the left-to-right extrema can be computed as 1/mean(time between extrema). During walking or running, the ratio of the two frequencies will be approximately 1, and this criteria can be used to detect walking or running.

Figure 27:
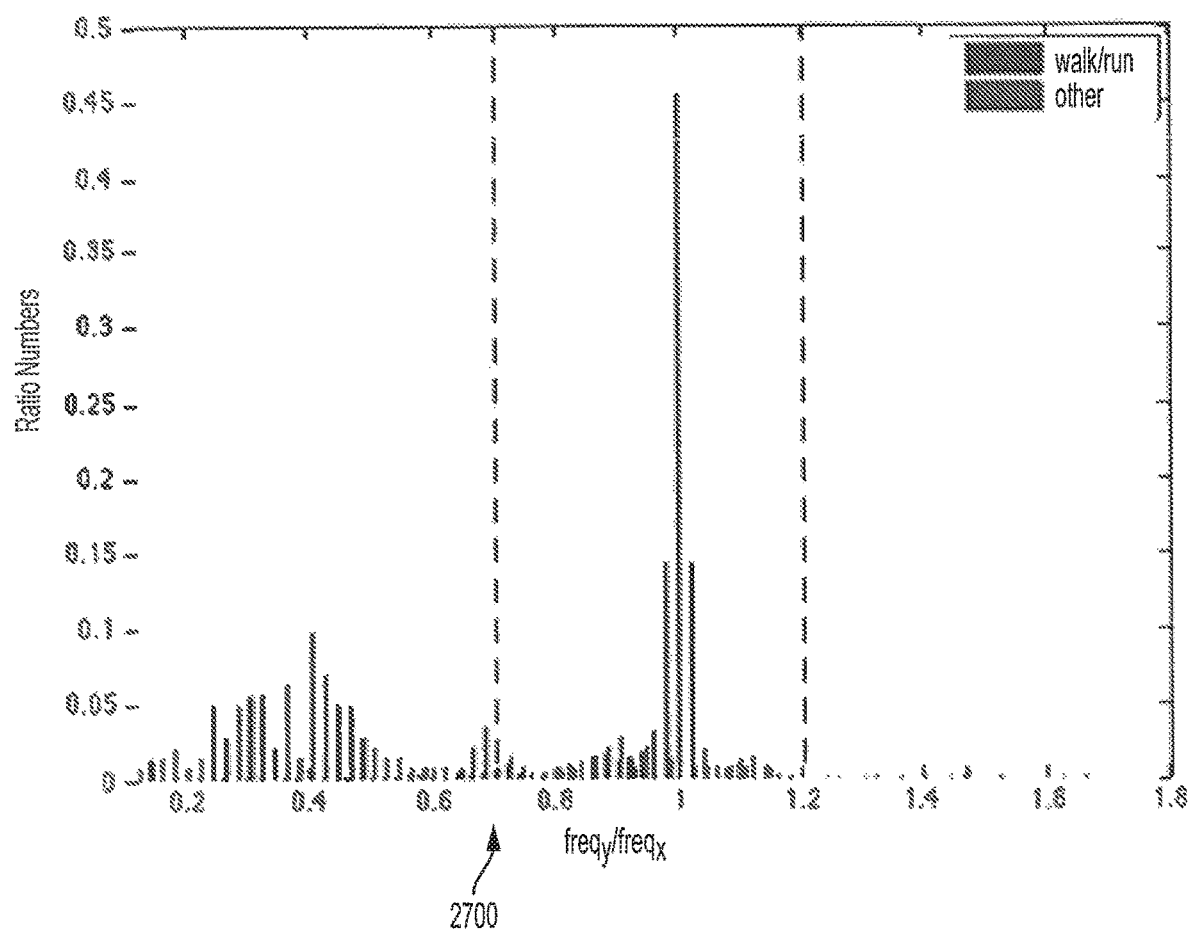
FIG. 27 illustrates a graph showing a Ratio of frequencies in the vertical and left-right directions in accordance with an embodiment.

FIG. 27 illustrates a graph 2700 showing a ratio of frequencies in the vertical and left-right directions in accordance with an embodiment.

Figure 28:
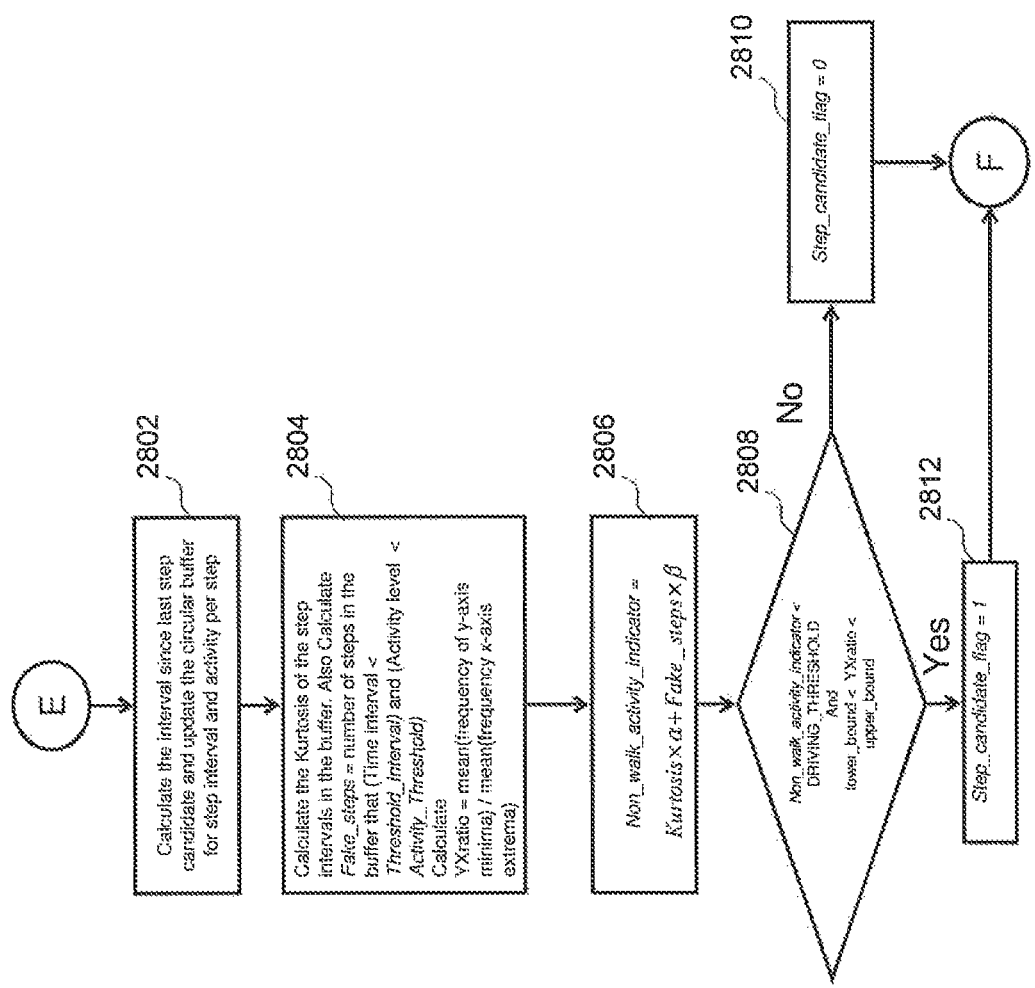
FIG. 28 illustrates a method for detecting activity in accordance with an embodiment.

FIG. 28 illustrates a method for detecting activity in accordance with an embodiment. Referring to FIGS. 18 and 28, the flow chart of FIG. 28 corresponds to step 1820 (Sporadic Movement Detection Algorithm) of the flow chart of FIG. 18.

Referring to FIG. 28, the wireless sensor device 100 calculates the interval since last step candidate, and updates the circular buffer for step interval and activity per step, via step 2802.

The wireless sensor device 100 then calculates the Kurtosis of the step intervals in the buffer, calculates fake steps=number of steps in the buffer that (Time interval<Threshold_Interval) and (Activity level<Activity_Threshold), and calculates YXratio=mean (frequency of y-axis minima)/mean(frequency x-axis extrema), via step 2804.

The wireless sensor device 100 sets the non_walk_activity_indicator=Kurtosis×a+fake_steps×b, via step 2806.

The wireless sensor device 100 determines if a non-walk activity indicator<a driving threshold, and determines if a lower_bound<YXratio<upper_bound, via step 2808. If not, the wireless sensor device 100 sets a step candidate flag=0, via step 2810. If yes, the wireless sensor device 100 sets a step candidate flag=1, via step 2812.

Embodiments disclosed herein provide numerous benefits. For example, implementations of the embodiments described herein use a wireless sensor device such as an accelerometer that is mounted on the chest or torso of a person to determine body postures and activities.

As described herein, embodiments provide a method and system for determining body postures and activities of a person. As described in more detail below, a body sensor device receives sensor data. The body sensor device then detects and classifies a body transition of a body based on the sensor data. The body sensor device then detects if there is activity of the body based on the sensor data. If there is activity, the body sensor device classifies the activity. If there is no activity, the body sensor device classifies a rest position of the body based on the sensor data and based on a previous body transition.

A method and system for determining body postures and activities of a person has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable medium providing program code for use by or in connection with a computer or any instruction execution system. For the purposes of this description, a computer-usable or computer-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a computer-readable medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments, and those variations would be within the spirit and scope of the present invention. Accordingly, many modifications may be made by one of ordinary skill in the art without departing from the spirit and scope of the appended claims.

What is claimed is:

1. A computer-implemented method for determining body postures and activities, the method comprising:
   receiving sensor data using a body sensor device;
   calibrating the sensor data to get rotated accelerations in the calibrated axes;
   calculating a transition signal from the calibrated sensor data;
   detecting and classifying transition of a body if the transition signal exceeds a transition threshold, wherein classifying transition of the body comprises:
      finding extrema and extrema timings in Y and Z acceleration signals;
      calculating features as functions of signal area estimations surrounding detected extrema in Y and Z acceleration signals;
      comparing extrema to a predetermined threshold to reject artifacts;
      identifying transition as unknown activity in case of features identified as potential artifacts;
      classifying transition as any of stand-to-sit, sit-to-stand, bend based on distances calculated using classification model weights;
   determining if there is activity of the body based on the sensor data;
   classifying the activity if there is activity; and classifying a rest position of the body if there is no activity, based on the sensor data and based on the detected body transition.

2. The method of claim 1, wherein calibrating the sensor data to get rotated accelerations includes matching axes of the sensor with axes of the body.

3. The method of claim 1, wherein the detecting of the body transition comprises detecting if the body is transitioning from a first body position to a second body position.

4. The method of claim 1, wherein the detecting if there is activity of the body comprises:
   determining a signal magnitude area of the accelerometer signals;
   determining if the signal magnitude area is greater than an activity threshold;
   and determining that there is activity of the body if the signal magnitude area is greater than the activity threshold.

5. The method of claim 1, wherein the activity is one of walking or running.

6. The method of claim 1, wherein the classifying of the rest position of the body comprises:
   computing a vertical angle; and
   classifying the rest position based on the vertical angle and a previous body transition.

7. The method of claim 1, wherein the rest position is one of sitting, standing, or lying down.

8. A body sensor device for determining body postures and activities, the body sensor device comprising:
   a sensor;
   a processor; and
   a memory coupled to the processor, wherein the body sensor device includes an application that, when executed by the processor, causes the processor to perform operations comprising:
   receiving sensor data using the body sensor device; calibrating the sensor data to get rotated accelerations in the calibrated axes;
   calculating a transition signal from the calibrated sensor data;
   detecting and classifying transition of a body if the transition signal exceeds a transition threshold, wherein the classifying transition of a body comprises:
      finding extrema and extrema timings in Y and Z acceleration signals;
      calculating features as functions of signal area estimations surrounding detected extrema in Y and Z acceleration signals;
      comparing extrema to a predetermined threshold to reject artifacts;
      identifying transition as unknown activity in case of features identified as potential artifacts;
      classifying transition as any of stand-to-sit, sit-to-stand, bend based on distances calculated using classification model weights;
   determining if there is activity of the body based on the sensor data;
   classifying the activity if there is activity; and
   if there is no activity, classifying a rest position of the body if there is no activity, based on the sensor data and based on the detected body transition.

9. The body sensor device of claim 8, wherein the operations comprising calibrating the sensor data to get rotated accelerations includes matching axes of the sensor with axes of the body.

10. The body sensor device of claim 8, wherein the detecting of the body transition comprises detecting if the body is transitioning from a first body position to a second body position.

11. The body sensor device of claim 8, wherein the detecting if there is activity of the body comprises:
   determining a signal magnitude area of accelerometer signals;

determining if the signal magnitude area is greater than an activity threshold;

and determining that there is activity of the body if the signal magnitude area is greater than the activity threshold.

12. The body sensor device of claim 8, wherein the activity is one of walking or running.

13. The body sensor device of claim 8, wherein the classifying of the rest position of the body comprises:

computing a vertical angle; and classifying the rest position based on the vertical angle and a previous body transition.

14. The body sensor device of claim 8, wherein the rest position is sitting.

15. The body sensor device of claim 8, wherein the rest position is standing.

16. The body sensor device of claim 8, wherein the rest position is lying down.

\* \* \* \* \*